United States Patent
Dein

(10) Patent No.: US 9,168,104 B2
(45) Date of Patent: Oct. 27, 2015

(54) INTRA-OPERATIVE SYSTEM FOR IDENTIFYING AND TRACKING SURGICAL SHARP OBJECTS, INSTRUMENTS, AND SPONGES

(76) Inventor: John Richard Dein, Fair Oaks, CA (US)

( * ) Notice: Subject to any disclaimer, the term of this patent is extended or adjusted under 35 U.S.C. 154(b) by 1227 days.

(21) Appl. No.: 12/490,140

(22) Filed: Jun. 23, 2009

(65) Prior Publication Data

US 2009/0317002 A1 Dec. 24, 2009

Related U.S. Application Data

(60) Provisional application No. 61/198,211, filed on Nov. 3, 2008, provisional application No. 61/132,954, filed on Jun. 24, 2008, provisional application No. 61/132,961, filed on Jun. 23, 2008.

(51) Int. Cl.
*G06K 9/00* (2006.01)
*A61B 19/00* (2006.01)
*A61B 19/08* (2006.01)

(52) U.S. Cl.
CPC ............... *A61B 19/44* (2013.01); *A61B 19/081* (2013.01); *A61B 19/5225* (2013.01); *A61B 2019/442* (2013.01); *A61B 2019/446* (2013.01); *A61B 2019/448* (2013.01)

(58) Field of Classification Search
USPC .................................. 382/103, 128, 321, 190
See application file for complete search history.

(56) References Cited

U.S. PATENT DOCUMENTS

| | | | |
|---|---|---|---|
| 4,490,848 A * | 12/1984 | Beall et al. ................... 382/152 |
| 4,943,939 A | 7/1990 | Hoover | |
| 5,374,813 A * | 12/1994 | Shipp ............................ 235/375 |
| 5,456,718 A | 10/1995 | Szymaitis | |
| 5,463,213 A * | 10/1995 | Honda ........................... 235/468 |
| 5,610,811 A * | 3/1997 | Honda ............................... 705/2 |
| 5,629,498 A | 5/1997 | Pollock et al. | |
| 5,637,850 A * | 6/1997 | Honda ........................... 235/454 |
| 5,650,596 A | 7/1997 | Morris et al. | |
| 5,678,569 A | 10/1997 | Chew et al. | |
| 5,923,001 A | 7/1999 | Morris et al. | |
| 5,931,824 A | 8/1999 | Stewart et al. | |
| 5,996,889 A * | 12/1999 | Fuchs et al. ................... 235/375 |

(Continued)

FOREIGN PATENT DOCUMENTS

WO 03073934 9/2003

OTHER PUBLICATIONS

Adaptive document image binarization, Sauvola et al., Elsevier, Pattern recognition 33, 2000, pp. 225-236.*

(Continued)

*Primary Examiner* — Jayesh A Patel
(74) *Attorney, Agent, or Firm* — Bret E. Field; Bozicevic, Field & Francis LLP

(57) ABSTRACT

Intra-operative systems for identifying surgical sharp objects are provided. Aspects of the systems include an intra-operative imaging device for obtaining intra-operative surgical sharp object image data; and a surgical sharp object automated shape recognition module configured to identify a surgical sharp object from intra-operative surgical sharp object image data. Systems of the invention may further include additional components, such as surgical instrument and/or sponge identification and tracking devices. Systems of the invention find use in a variety of methods and applications, including tracking of surgical items during a surgical procedure.

19 Claims, 22 Drawing Sheets

(56) References Cited

U.S. PATENT DOCUMENTS

| | | | |
|---|---|---|---|
| 6,054,924 A | 4/2000 | Dames et al. | |
| 6,123,185 A | 9/2000 | Demarest et al. | |
| 6,216,029 B1 * | 4/2001 | Paltieli | 600/427 |
| 6,230,972 B1 | 5/2001 | Dames et al. | |
| 6,371,379 B1 | 4/2002 | Dames et al. | |
| 6,644,464 B1 | 11/2003 | Demarest et al. | |
| 6,690,964 B2 * | 2/2004 | Bieger et al. | 600/424 |
| 6,777,623 B2 | 8/2004 | Ballard | |
| 6,973,202 B2 * | 12/2005 | Mostafavi | 382/103 |
| 6,997,305 B2 | 2/2006 | Demarest et al. | |
| 6,998,541 B2 | 2/2006 | Morris et al. | |
| 7,118,029 B2 | 10/2006 | Nycz et al. | |
| 7,164,968 B2 | 1/2007 | Treat et al. | |
| 7,180,014 B2 * | 2/2007 | Farber et al. | 177/25.19 |
| 7,256,696 B2 * | 8/2007 | Levin | 340/572.1 |
| 7,307,530 B2 | 12/2007 | Fabian et al. | |
| 7,362,228 B2 * | 4/2008 | Nycz et al. | 340/572.1 |
| 7,411,506 B2 | 8/2008 | Volpi et al. | |
| 7,420,468 B2 | 9/2008 | Fabian et al. | |
| 7,518,502 B2 * | 4/2009 | Austin et al. | 340/539.1 |
| 7,562,025 B2 * | 7/2009 | Mallett et al. | 705/308 |
| 7,677,395 B2 * | 3/2010 | Bennett et al. | 209/552 |
| 7,809,184 B2 * | 10/2010 | Neubauer et al. | 382/154 |
| 8,544,751 B2 * | 10/2013 | Jamali et al. | 235/487 |
| 2002/0067263 A1 * | 6/2002 | Tafoya et al. | 340/572.1 |
| 2002/0116254 A1 * | 8/2002 | Stein et al. | 705/11 |
| 2003/0192722 A1 | 10/2003 | Ballard | |
| 2005/0015311 A1 * | 1/2005 | Frantz et al. | 705/26 |
| 2005/0016776 A1 | 1/2005 | Ballard | |
| 2005/0075564 A1 * | 4/2005 | Ballard | 600/436 |
| 2005/0131578 A1 * | 6/2005 | Weaver | 700/244 |
| 2005/0199645 A1 * | 9/2005 | Sivertsen et al. | 221/221 |
| 2005/0203470 A1 * | 9/2005 | Ballard | 604/362 |
| 2005/0279368 A1 | 12/2005 | McCombs | |
| 2006/0138211 A1 * | 6/2006 | Lubow | 235/375 |
| 2006/0212306 A1 * | 9/2006 | Mallett et al. | 705/1 |
| 2006/0226957 A1 * | 10/2006 | Miller et al. | 340/286.07 |
| 2007/0080223 A1 * | 4/2007 | Japuntich | 235/439 |
| 2007/0083170 A1 | 4/2007 | Stewart et al. | |
| 2007/0167801 A1 * | 7/2007 | Webler et al. | 600/459 |
| 2007/0225550 A1 * | 9/2007 | Gattani et al. | 600/101 |
| 2007/0268133 A1 * | 11/2007 | Sanchez et al. | 340/568.1 |
| 2007/0285249 A1 * | 12/2007 | Blair et al. | 340/572.3 |
| 2008/0051746 A1 * | 2/2008 | Shen-Gunther | 604/362 |
| 2008/0091221 A1 | 4/2008 | Brubaker et al. | |

OTHER PUBLICATIONS

Radio frequency—sponges, Rogers et al., Springer, Surgical endoscopy, 2007, pp. 1235-1237.*

Assist—Automated system—Tracking, Rivera et al., IEEE, 978-1-4244-1712-4, Apr. 16-17, 2008, pp. 297-302.*

GPU based real-time—ultrasound, Novotny et al, Elsevier, 1361-8415, 2007, pp. 458-464.*

\* cited by examiner

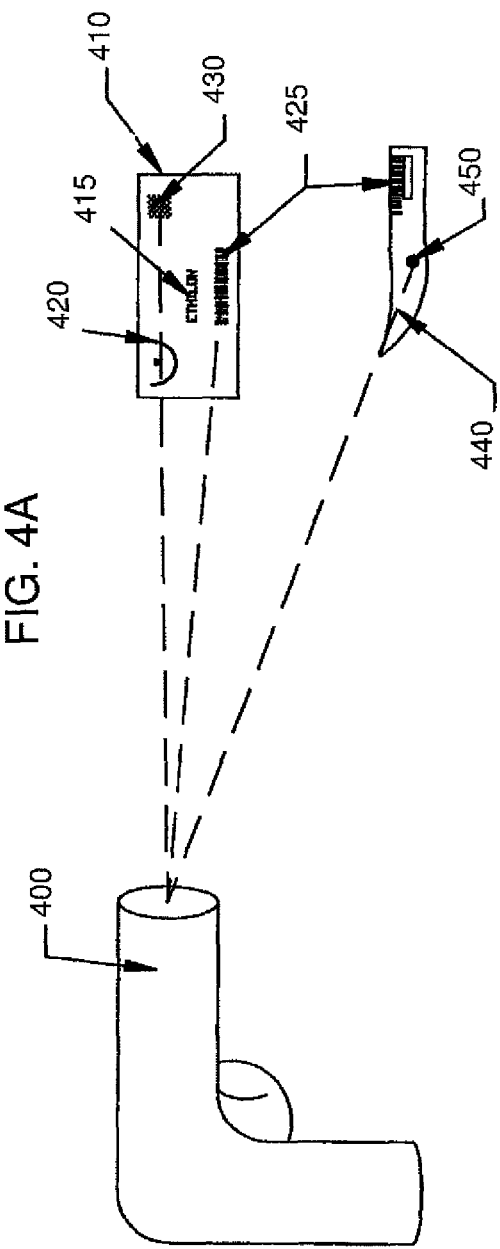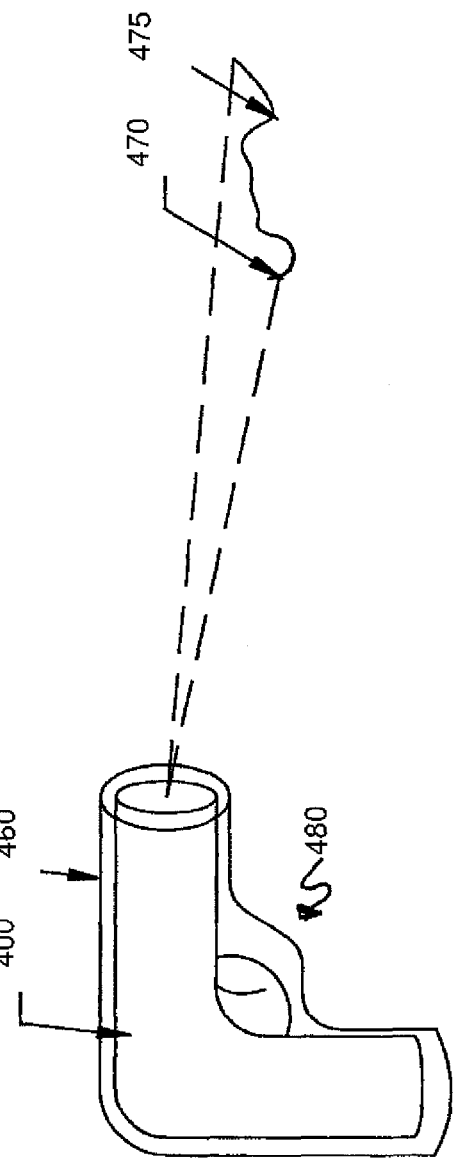

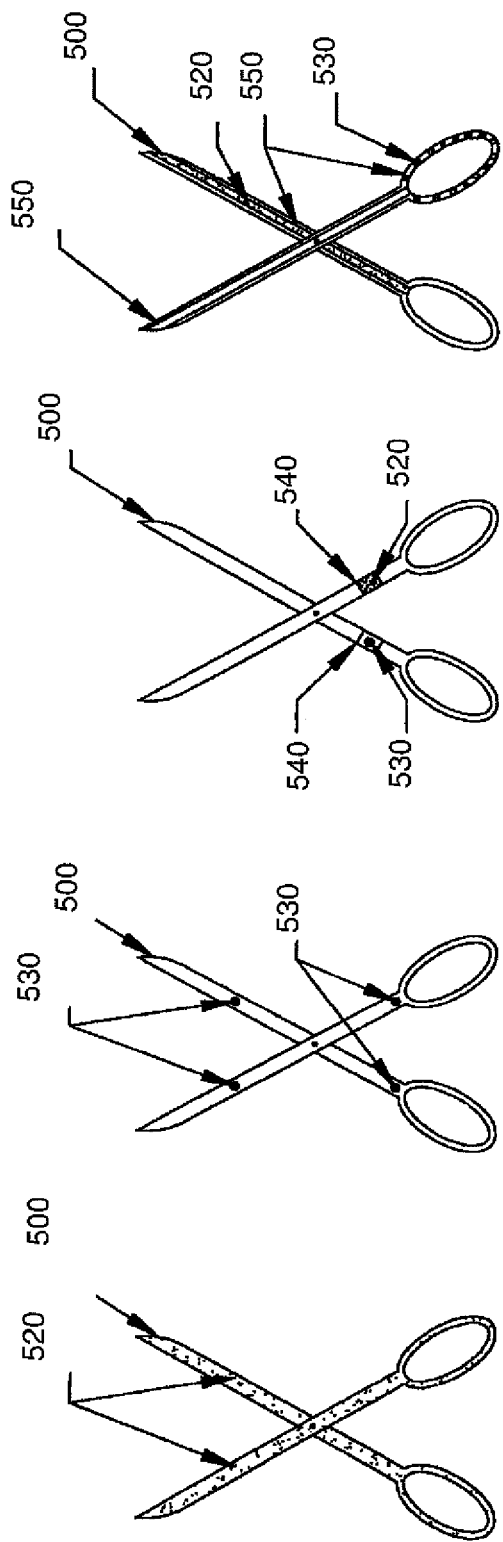

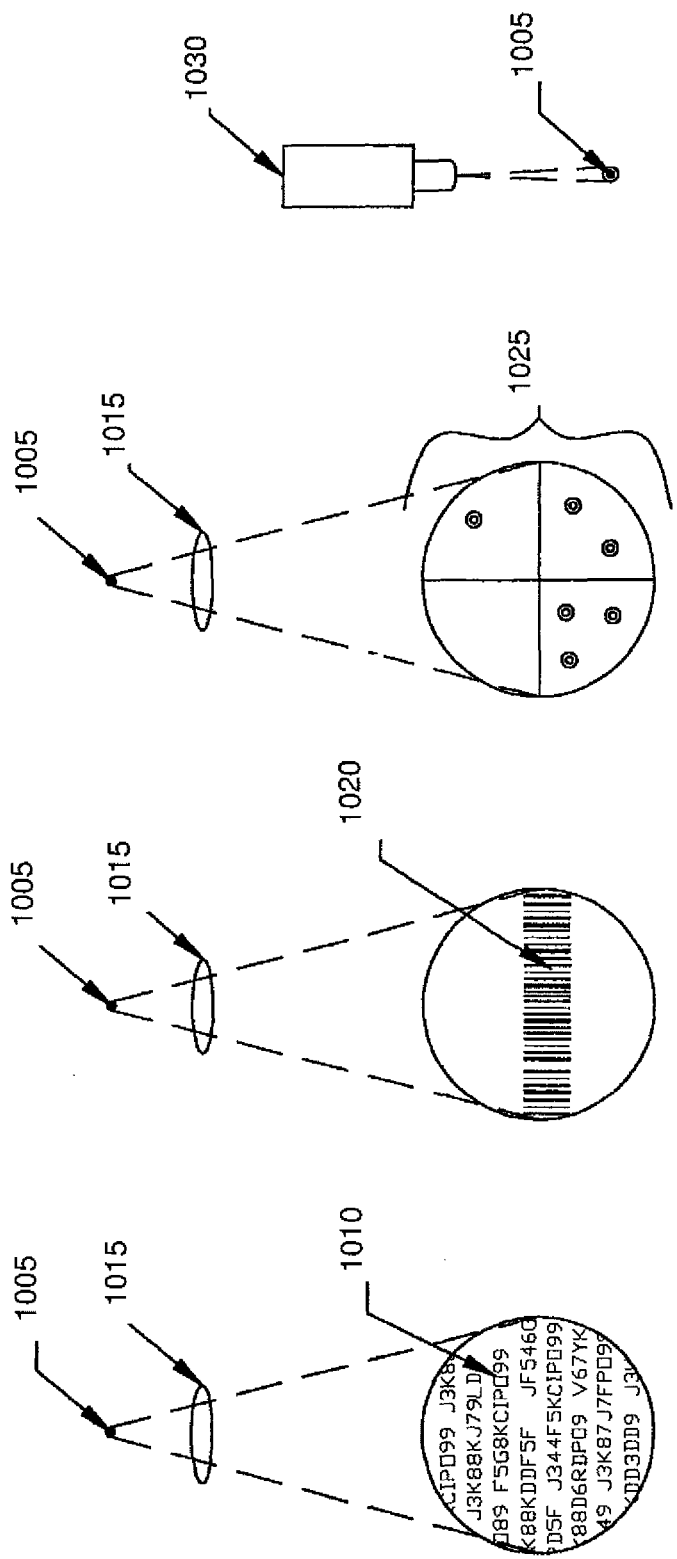

|  | TIME |
| --- | --- |
| NEEDLES | 12:00:00 |
| SHARPS | 12:00:00 |

IN     OFF
 x      Y

ALL ACCOUNTED FOR?
VERIFY   YES ☐   NO ☐
PERSONNEL CODE: SCRUB___ CIRCULATOR___

|  | IN | OUT | TOTAL | TIME |
|---|---|---|---|---|
| SPONGES | x | Y | Z | 12:00:00 |
| INSTRUMENTS | x | Y | Z | |
| SHARPS | x | Y | Z | |

ALL ACCOUNTED FOR?
VERIFY   YES ☐   NO ☐
PERSONNEL CODE _____

INTRA-OPERATIVE SYSTEM FOR IDENTIFYING AND TRACKING SURGICAL SHARP OBJECTS, INSTRUMENTS, AND SPONGES

CROSS-REFERENCE To RELATED APPLICATIONS

Pursuant to 35 U.S.C. §119(e), this application claims priority to the filing date of the U.S. Provisional Patent Application Ser. No. 61/132,961 filed Jun. 23, 2008; to the filing date of the U.S. Provisional Patent Application Ser. No. 61/132,954 filed Jun. 24, 2008 and to the filing date of U.S. Provisional Application Ser. No. 61/198,211 filed Nov. 3, 2008; the disclosures of which applications are herein incorporated by reference.

INTRODUCTION

It has been estimated that in the United States alone some 25 million operations are performed annually and most involve the use of multiple surgical items, including needles and other sharp objects, surgical sponges, and surgical instruments. These various items can be retained unintentionally within patients at the conclusion of a given operation. A retained surgical foreign body (RSFB) usually requires at least a second surgery for retrieval of the object, and also carries a risk for major complications including death. The prevalence of retained foreign bodies is not known, though one medical malpractice insurance company reported approximately 40 cases over 7 years or about 1% of all claims (Kaiser C W, Friedman S, Spurling K P, Slowick T, Kaiser H A. The retained surgical sponge Ann Surg 1996:224:79-84). One review cited prevalence as high as 1/5000 cases with an associated mortality ranging from 11 to 35% (Lauwers P R, Van Hee R H. Intraperitoneal gossypibomas: The need to count sponges; World J Surg 2000:24: 521-527).

The Association of Perioperative Registered Nurses (AORN) recommends that counts be performed before each procedure to establish a baseline, before closure of any cavity such as the stomach or a cardiac chamber, before wound closure begins, at end of skin closure or the end of the procedure, and at the time of any permanent change in operating room personnel (Recommended practices for sponge, sharp, and instrument counts. AORN Recommended Practices Committee. Association of PeriOperative Registered Nurses. AORN J 1999:70: 1083-9). It is recommended that more than one person do the counts in a standard order, simultaneously and audibly, and with minimal interruptions. In practice, each of the multiple counts usually takes 15-30 minutes and often slows or stops the operation.

In most cases of RSFB, manual counts indicated that all equipment was accounted for, leading to the conclusion that the counts must have been incorrect (Gawande A, et al. Risk factors for retained instruments and sponges after surgery New Engl J Med 348:229 C235, January 2003). About 88% of RSFB incidents occur when the count is thought to be correct. Furthermore, Medicare announced in October 2008 that there will be no hospital payment for RSFB. Possible causes for incorrect counts include staff fatigue, stress, distraction, interruptions, time pressure, and simple human errors in counting and recording.

Therefore, there is a need for improved systems and methods for identifying and tracking surgical items, including needles and other sharp objects, surgical sponges, and surgical instruments during a surgical procedure.

SUMMARY

Intra-operative systems for identifying surgical sharp objects are provided. Aspects of the systems include an intra-operative imaging device for obtaining intra-operative surgical sharp object image data; and a surgical sharp object automated shape recognition module configured to identify a surgical sharp object from intra-operative surgical sharp object image data. Systems of the invention may further include additional components, such as surgical instrument and/or sponge identification and tracking devices. Systems of the invention find use in a variety of methods and applications, including tracking of surgical items during a surgical procedure.

BRIEF DESCRIPTION OF THE FIGURES

FIGS. 4A and 4B provide a view of an embodiment of a unique identifier recognition system that can be used to detect or recognize a unique identifier on a needle or sharp object or its packaging.

FIGS. 5B to 5E provide additional views of a surgical instrument with various unique identifiers in accordance with embodiments of the invention.

FIGS. 10A-10C are magnified schematic views of various unique identifiers that can be placed on a sponge, instrument or needle or other sharp item in accordance with embodiments of the invention.

FIG. 10D is a view of a detector detecting a unique identifier in accordance with an embodiment of the invention.

FIG. 17 is another schematic of a large panel display of a real-time needle and sharp object count indicating the presence or absence of the items at any time during the surgical procedure, according to an embodiment of the invention.

FIG. 18 is another schematic of a large panel display of a real-time needle and sharp object count indicating the presence or absence of any sponge, instrument or needle/sharp object at any time during the surgical procedure, according to an embodiment of the invention.

DETAILED DESCRIPTION

Figure 1A:
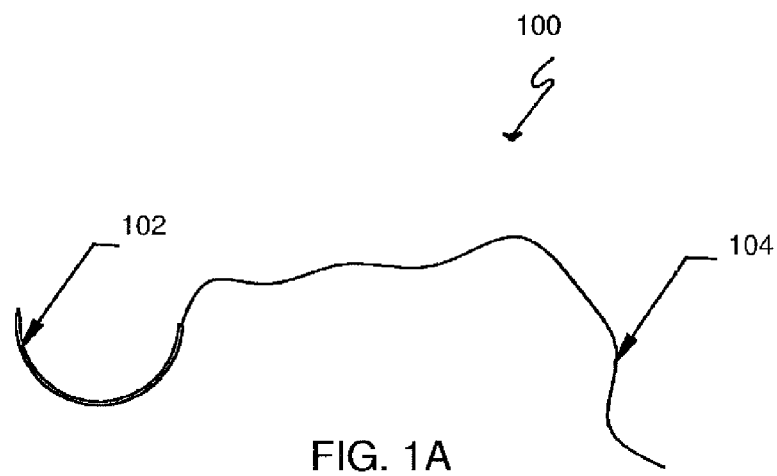
FIGS. 1A and 1B provide views of a surgical sharp object and a handheld imager configured to recognize the surgical sharp object via shape recognition, according to an embodiment of the invention.

Intra-operative systems for identifying surgical sharp objects are provided. Aspects of the systems include an intra-operative imaging device for obtaining intra-operative surgical sharp object image data; and a surgical sharp object automated shape recognition module configured to identify a surgical sharp object from intra-operative surgical sharp object image data. Systems of the invention may further include additional components, such as surgical instrument and/or sponge identification and tracking devices. Systems of the invention find use in a variety of methods and applications, including tracking of surgical items during a surgical procedure.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the module of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing various aspects of the invention, the systems will be described first in greater detail, followed by a review of methods and applications in which the systems find use.

Systems

As summarized above, systems for intra-operatively identifying a surgical sharp object are provided. By surgical sharp object is meant an object that has one or more sharp features and is configured to contact tissue during a surgical procedure. As the objects have one or more sharp features, the objects identified by systems of the invention include a thin cutting edge or a fine point, such that the objects are well-adapted for cutting or piercing tissue. Examples of surgical sharp objects include, but are not limited to, needles, scalpel blades, etc. In some instances, surgical sharp objects are objects that are configured for one time use, such that they are to be disposed of following their use in a given surgical procedure, and in some embodiment surgical sharp objects are reusable.

As indicated above, the systems are systems of intra-operatively identifying surgical sharp objects. By intra-operatively identifying is meant that the systems are configured to identify a surgical sharp object during a surgical procedure, where the identification may be made in or out of the sterile field, but in certain instances the identification is made in the room where a given surgical procedure is performed. By surgical procedure is meant an operation, including an open surgical procedure, or a minimally-invasive surgical procedure, including endoscopic procedures, such that there is at least one opening into a body where a foreign body could be unintentionally left inside of a body. A surgical procedure can include the actual procedure itself, as well as the period of time during preparation for and after the conclusion of the surgical procedure (e.g., performing initial or final counting and identification of a surgical sharp object, etc.) As the systems are systems for identifying surgical sharp objects, they are systems that are configured to recognize or establish a given object as a particular surgical sharp object, such that the systems provide verification of the identity of a given surgical sharp object.

Intra-Operative Imaging Device and Automated Shape Recognition Module

Systems of invention include an intra-operative imaging device and an automated shape recognition module. By intra-operative imaging device is meant a device that is configured to obtain intra-operative surgical sharp object image data. In other words, the device is configured to obtain image data of a surgical sharp object in an operating room. Accordingly, this imaging device of the system is located in an operating room.

The intra-operative imaging device may vary depending on the nature of the image data that the system is configured to employ. The image data may be data for one or more still images, or video data. Any convenient intra-operative imaging device configured to obtain such data may be employed, where examples of such systems include digital or analog still cameras, digital or analog video cameras, etc. Where the imaging device is a camera, the camera can include one or more lenses for optimal focus of the desired field of view onto an image sensor of the camera. The camera can be black and white, or color, and can be digital, or analog. The camera may be configured to obtain still or video image data. In some embodiments, the camera can include a processor. In some embodiments, a camera with a processor can be used in addition to a CPU of the system, e.g., as reviewed in greater detail below. The contain may further include one or more light sources, a synchronizing sensor, and input/output hardware or communication links with other components of a system to report results (e.g., via a display unit, such as a monitor). Cameras that can be used in the methods of the subject invention include, but are not limited to: the Cognex™ Insight Micro Smart Camera™ with Insight-Explorer™ Vision software, Sick™ Smart camera IVC-2D used with IVC Studio™ software, National Instrument™ Smart Camera with NI Vision Builder™ AI program, Sony XCI Camera™ with any suitable machine vision cameras and programs sold by Dalsa™, Visionx™, Matrox™ Imaging, etc., or any other suitable camera.

The intra-operative imaging device is a device configured to obtain image data of a given surgical sharp object, and then output that obtained image data. Examples of specific types of intra-operative imaging devices and systems that include the same are reviewed in greater detail below.

In addition to the intra-operative imaging device, the systems include a surgical sharp object automated shape recognition module. This surgical sharp object automated shape recognition module is a functional module that is configured to identify a surgical sharp object from intra-operative surgical sharp image data obtained by the intra-operative imaging device, e.g., as described above. The term "module" refers to a combination of hardware and/or software which is configured to perform a specific given function or functions. For example, a given module may be a programmable digital microprocessor such as available in the form of an electronic controller, mainframe, server or personal computer (desktop or portable). Where the module is programmable, suitable programming can be communicated from a remote location to the module, or previously saved in a computer program product (such as a portable or fixed computer readable storage medium, whether magnetic, optical or solid state device based). For example, a magnetic medium or optical disk may carry the programming, and can be read by a suitable reader communicating with a given module at its corresponding station.

Surgical sharp object automated shape recognition modules are modules that are configured to identify a surgical sharp object, such as a needle or scalpel blade, without the need for an identifying label (examples of which are described in greater detail below) by a method of automated shape recognition, such as machine vision. Automated shape recognition is a process by which the identification of surgical sharp objects is performed using one or more of the size, shape, aspect ratio, outline, color, or other distinctive feature present in the image data of the surgical sharp object. Automated shape recognition can be performed in two-dimensions or three-dimensions. For example, a digital camera (either gray-scale or color vision camera) can obtain image data of a surgical sharp object, which image data can then be processed by the automated shape recognition module (and specifically by software and/or hardware of the module) using a machine vision and image processing technique.

Any convenient machine vision and image processing technique may be employed. To distinguish between specific surgical sharp objects such as a scalpel and a needle, the module may use variables such as the size, shape, aspect ratio, outline, or color of the of the sharp object, certain angles or curves, the two-dimensional projection that is unique to a given surgical sharp object, etc. For example, the curve formed by a certain size of surgical needle can be used to identify the needle via automated shape recognition protocols.

The software can take several steps to process an image. The image may first be manipulated to reduce noise or to convert many shades of gray to a simple combination of black and white (binarization). Following the initial simplification, the software may count and/or identify objects in the image. Any suitable software program can be used, including commercially available software programs, as disclosed above, are available and can be used in one embodiment of the invention. The methods can include use of a software program to process images and detect relevant features for identifying a surgical item.

A given automated shape recognition module may employ pre-existing surgical sharp object data in a given automated shape recognition protocol, e.g., a reference with which to compare the obtained image data in order to identify a given surgical sharp object. This pre-existing surgical sharp object data may be provided in the shape recognition module using a variety of different protocols. For example, the pre-existing surgical sharp object data may be introduced into the shape recognition module at the time of manufacture, where the data may or may not be updatable depending on the nature of the particular module. Alternatively, prior to the beginning of a given surgical procedure, the data about the specific surgical sharp objects (and other items as desired) which are to be identified using automated shape recognition (i.e., machine vision) are programmed into the software. For example, in an aortic valve replacement procedure, the types of needles to be used may include Ethicon™ 2-0 silk SH, Ethicon™ 0 Vicry™ CTX-B, Deknatel™ Tevdek® II 3-0 AT-2, Ethicon™ Prolene™ 4-0 RB-1, Ethicon™ Prolene™ 6-0 BV Ethibond™ Excel™ 2-0 SH, and Ethicon™ Prolene™ 7-0 BV-1 needles. These seven different types of needles can be programmed into the system prior to the start of surgery. The number of needles that can be programmed into a system will vary depending on the system, but can be at least two or more, such as three or more, or four or more, etc. This data regarding the types of needles may be introduced into the shape recognition module using any convenient protocol, where protocols of interest include both manual and automatic protocols, e.g., as described in greater detail below.

In some embodiments, the pre-programmed information can include information saved in the computer memory for a particular type of surgery (e.g., appendectomy, or knee replacement) which can be recalled as needed. In some embodiments, the pre-programmed information saved in the computer memory can include both the type of surgery as well as information specific to a particular surgeon, to reflect the needle or other surgical sharp item preferences of a specific surgeon.

Machine vision software programs that can be used for automated shape identification can use a number of different image processing techniques for identification of an object, such as pixel counting (counts the number of light or dark pixels), thresholding (converts an image with gray tones to simply black and white), segmentation (used to locate and/or count parts), pattern recognition (location of an object that may be rotated, partially hidden by another object, or varying in size), detection of particular angle or curve, measurement of area or size of an object, determining the aspect ratio of the object, edge detection, the outline or silhouette detection, the two- or three-dimensional projection of an object, template matching, color, etc. Examples of machine vision software programs that can be used with the subject invention include but are not limited to Insight-Explorer™ Vision software, IVC Studio™ software, National Instrument™ Vision Builder™ software, any suitable software programs sold by Dalsa™, Visionx™, Matrox™ Imaging, etc., or any other suitable machine vision software program. Also, in some embodiments, "template matching" of the outline or silhouette of a surgical sharp object is used by a given shape recognition module to distinguish one surgical sharp object from another.

In some embodiments, the machine vision methods can use a combination of processing techniques to identify an object; for example, the detection of a particular curve and the measured size may be used to identify a particular needle. As such, more than one identification technique can be used in order to improve the accuracy and reliability of the identification process. For example, in some embodiments, an optional algorithm can be included for evaluating the remnant of suture material still attached to a needle. This can include evaluating characteristics of the suture, for example, if silk suture is black and Prolene™ suture is blue, identifying the color of the attached suture can assist in the identification of the needle, especially in cases where a needle might be bent, twisted or broken. In some embodiments, the shape recognition module is configured to keep track of the accuracy rate of the various techniques used, and if certain techniques are more successful, those techniques could be given greater weight in the recognition process.

In one embodiment of the invention, the automated shape recognition module can contain a database of the observed values for the various characteristics used to identify various surgical sharp objects, as well as other surgical items of interest, as desired. For example, depending on slight variations in ambient lighting and also in the surface optical characteristics of e.g., a surgical needle, there might be some variation in the perceived size of a surgical sharp object by the automated shape recognition module. In some embodiments, therefore, the system can maintain a data set, e.g., in the form of a table or histogram, of the number of times a particular measurement of size or other characteristic (e.g., needle curvature) was associated with a particular surgical item. The system can employ statistical techniques to determine the probability that a measured size or shape can be accurately associated with that particular surgical item. In some instances, given such a data base of several characteristics, multivariate statistical analysis is performed to increase accuracy and reliability of the system in identifying the surgical sharp objects.

In some embodiments, if the automated shape recognition module is unable to make a positive identification of a needle, the automated shape recognition module can include an "assisted identification" algorithm which can present a choice to operating room personnel, who can then positively identify the surgical sharp object that has been discarded. For example, if a needle is bent, the automated shape recognition module can narrow the identification of the needle to two options, e.g an Ethicon™ 8-0 BV-1 taper point needle or an Ethicon™ 7-0 CC tapercut needle. The choice of the two types of needles can be presented to a scrub nurse, who can select the needle which corresponds to the type of needle that was discarded.

It should be understood that the terms "automated shape recognition", "automated shape identification", and "machine vision", can all be used to indicate the automatic identification of surgical sharp objects (such as scalpel blades or needles) from one or more types of image data obtained for the object, e.g., one or more types of image data relating to the size, shape, aspect ratio, outline, color, or other imageable parameter of the surgical sharp object.

A given automated shape recognition module of a system may be configured to only provide shape recognition of surgical sharp objects. Alternatively, the shape recognition module may be configured to provide shape recognition of other surgical items, such as surgical instruments and/or sponges, in addition to the automated shape recognition of the surgical sharp object.

The location of the automated shape recognition module in the system may vary. For example, the automated shape recognition module may be located at a part of the system that is distinct from the intra-operative imaging device. In yet other embodiments, the imaging device and automated shape recognition module may be integrated into the same part or component of the system. In some embodiments the automated shape recognition module can be located in a sterile environment, and in other embodiments the automated shape recognition module can be located in a non-sterile environment. In some embodiments, the automated shape recognition module may be located in a transitional area between a sterile and non-sterile environment, e.g., as in the chute embodiment disclosed below.

Figure 1B:
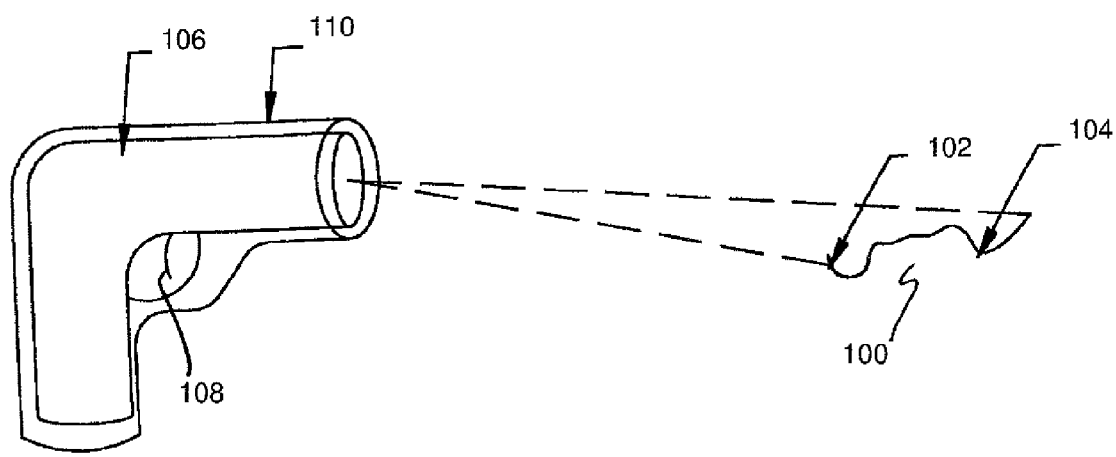

FIGS. 1A and 1B provide views of a surgical sharp object in the form of needle being imaged by a camera to obtain image data that may be used by an automated shape recognition module of a system of the invention to identify the needle. FIG. 1A shows needle/suture construct 100 that includes curved needle 102 and suture 104. As shown in FIG. 1B, needle imaging device 106 is a handheld camera that includes manual operation features 108 and sterile sleeve 110, which allows the camera to operate in a surgical sterile field. The automated shape recognition module may be integrated with the camera 106 or be present in another part of the system, as desired.

In another embodiment, the imaging device (and optionally the automated shape recognition module) may be part of a surgical sharp object disposal container. Surgical sharp object disposal containers can include one or more imaging devices, such as a camera with suitable optics for acquiring images, a camera interface for digitizing images (known as a "frame grabber") and, where desired, an automated shape recognition module (which can be an embedded processor, such as a digital signal processor (DSP), for example, as desired). In some embodiments, the container can further include a surgical sharp object automated tracking module, such that the container is configured to automatically track one or more surgical sharp objects, e.g., by counting the objects, etc. The container can therefore use an imaging device (such as a camera) to image the surgical sharp object to obtain image data. In certain instances, the container may then identify the surgical sharp object using the image data by automated shape recognition. The machine vision protocol implemented by the shape recognition module of the container can, in some embodiments, count only the newly added surgical sharp object present in a field of view, such as a sterile back table, or in the disposal container, etc. Tracking and counting of only the newly added surgical sharp object can be performed by continuous or intermittent imaging of a group of surgical sharp objects in a particular field of view. When a surgical sharp object is newly added to the field of view, comparison of an image obtained prior to the addition of the new sharp object with an image obtained after the addition of the new sharp object can result in discounting or subtracting out the prior counted needle shapes and/or positions in a given image, and does not recount them. Therefore, the machine vision protocol of the shape recognition module can be used to count only the most recently discarded object. In some embodiments, the automated shape recognition module can be used to identify and count all of the surgical items present in a field of view. For example, if a recount is necessary, all the surgical sharp objects present in a field of view can be identified and counted.

As indicated above, surgical sharp object disposal containers may include one or more suitable light sources, which can be specialized light sources such as a light-emitting diode (LED) illuminators, fluorescent or halogen lamps, etc. The lighting can be used to illuminate the surgical sharp object to be imaged, and can also be used to highlight features of interest and obscure or minimize the appearance of features that are not of interest (such as shadows or reflections). The lighting can be located in any suitable location, including on or near the camera, or on or under a surface or platform where the surgical item to be imaged is placed, including lighting that is "front-lit", "back-lit", direct on-axis lighting (DOAL), off-axis lighting, multi-axis lighting, etc.

The container may include a synchronizing sensor for detecting the presence of a surgical item to be identified, and determining when an object is in position to be evaluated. The synchronizing sensor can be any suitable sensor, such as an optical or magnetic sensor, where the sensor can trigger image acquisition and processing by the imaging device of the container. For example, the synchronizing sensor triggers the camera to image the object as it passes within the viewing range of the camera, and can also synchronize a lighting pulse to obtain a sharp image. In this embodiment the device can include dynamic shape recognition, i.e., shape recognition of a surgical item in motion as it is dropped into a container.

The container may also include a display unit for displaying identifying information of the surgical sharp object, as well as additional derived information, such as the current counts of the number and type of items that have been placed in the container. The display of the current number and type of items in the container can be in addition to other displays of current counts in the operating room, e.g. as provided by a system of the invention or otherwise. The display unit on the container can be mounted permanently or it can be removably associated with the container in any suitable location, such as on the top or side of the container.

The container may be configured for surgical sharp object disposal. Such containers may have a portion that is reusable and a portion that is disposable. For example, the container may include a first reusable portion that includes the imaging device, e.g., camera. This first reusable portion can be sterilizable (e.g., with a sterile covering), where desired. In addition to the first portion, the container may include a second portion configured to hold the discarded surgical sharp objects. This second portion can be separable from the first portion and can have a variety of different configurations, such as a disposable plastic bag, disposable rigid receptacle, etc. In some embodiments, a container may be entirely located within a sterile field (e.g., on top of a sterile back table), or it can be entirely located in a non-sterile field (e.g., on the floor of the operating room). In some embodiments, portions of the container can be both in a sterile field and in a non-sterile field (e.g., a container may have a opening with a chute which is configured to be on or in the sterile field, which leads to the remainder of the container which is positioned in a non-sterile portion of a room).

In some embodiments, the container can be configured to receive surgical items other than surgical sharp objects, in addition to the surgical sharp objects. Additional types of surgical items for which the container may be configured to receive include instruments, e.g., forceps, scissors, etc., as well as textile-based items, e.g., sponges. In some embodiments, the container can have the capability of identifying and counting more than one category of surgical item (e.g., both needles, and sponges). For containers designed for sponge disposal, the container can also have a scale which can enable the determination of pre-operative versus post-operative weight of the sponges. This weight data can provide estimates for operative fluid or blood loss from a patient.

Containers of interest may also include surgical sharp object displayers that promote identification of the surgical sharp objects (as well as other surgical items, where desired). Displayers may take a variety of configurations, such as a platform, either flat or inclined, which can, in some embodiments, be back-lit, or front-lit, have direct on-axis lighting (DOAL), off-axis lighting, multi-axis lighting, etc. or can have one or more mirrors or other reflective surfaces for optimal identification of the surgical sharp object or other surgical item. In some embodiments, the container can include mechanical separators that are configured to provide mechanical separation of the surgical sharp objects and other surgical items, such as features which isolate a newly added item from previously placed items. Separators configured for mechanical separation of counted from uncounted items can include, but are not limited to: manually triggered or automatic trap-door mechanisms; vertical or horizontal rotating or circulating drums, wheels, discs, or flaps; valves or flap mechanisms; screens; magnets; compressed air driven separators; suction separators; separation arms; use of motion such as shaking; etc. Power to the device may be provided using any convenient protocols, such as via an electrical cord, a sterile disposable lead such as used with a Bovie cord, or can be provided by an internal power source, such as a battery. The power source can be housed in a sterile case, covering, or sleeve.

Figure 2A:
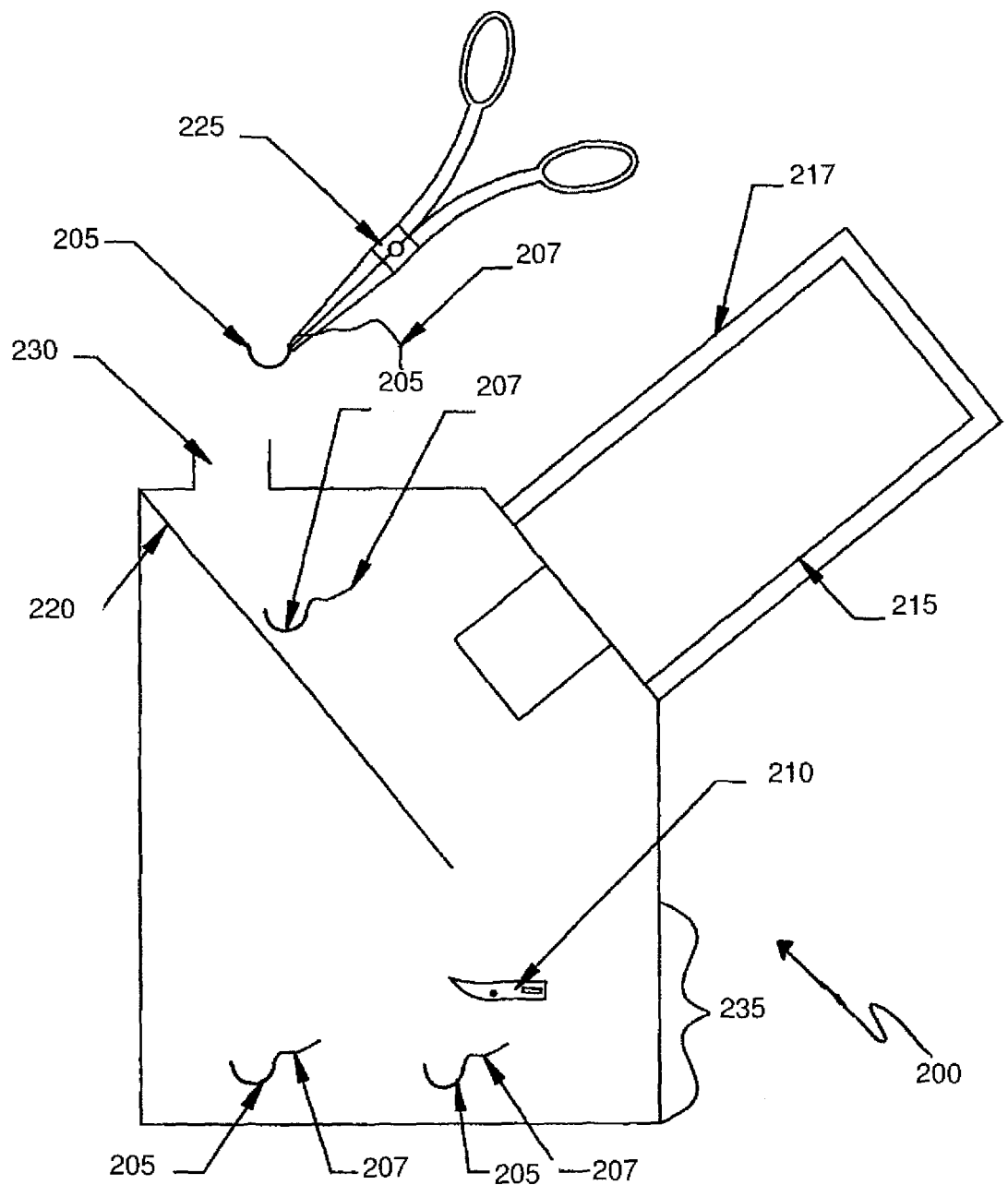
FIG. 2A is a schematic of a container for identification and disposal of a surgical sharp object, according to an embodiment of the invention.

FIG. 2A depicts one embodiment of a container configured to identify and dispose of a surgical sharp object. In FIG. 2A, container 200 is configured to identify and count a surgical sharp object, such as a needle 205 or other sharp object, such as a scalpel blade 210. Container 200 includes imaging device in the form of camera 215 that is activated by the act of disposal of the surgical sharp object (e.g., with a sync sensor (not shown)) to image the surgical sharp object (e.g., needle 205 or scalpel blade 210) as it is dropped into the container and goes past the camera's field of view. The automated shape recognition of the surgical sharp object can be performed dynamically as the sharp item slides down incline 220 by a high-speed optical detection imaging device 215 (e.g., a camera capable of capturing multiple images per second). In this embodiment, the high speed optical detection imaging device is camera 215 encased in a sterile case 217 and mounted onto a container configured to receive of and dispose of sharp surgical objects. During use, an operating room professional, such as a scrub nurse, can release a used needle 205 with the remnant of suture 207 from the needle holder 225 or other instrument into the container, without the need to manually manipulate the used needle. The needle 205 is released and allowed to drop into the chute 230 and onto an incline 220. As the presence of the dropped needle is sensed by a sensor (not shown), camera 215 enclosed within a sterile case 217 is activated to capture image data, e.g., in the form of a video or multiple still photos, as the sharp object slides down the incline 220. Camera 215 may be capable of capturing image data at many frames per second, which allows for identification of the shape of the particular needle 205, and in some embodiments, characteristics such as the texture, shape, or color of the associated suture 207. The image data obtained by the camera is compared by the system (e.g., in computer memory) to data representing the items that have been registered and counted as present at the operation. After identifying the surgical sharp object, the system counts the discarded item out of the operation (e.g., "checked out").

After dynamic automated shape recognition of the surgical sharp object as it slides down the incline 220, the counted item falls into the lower chamber 235 of the disposal device containing the previously counted and discarded items. Once the needle is inside the container, no further human contact with the sharp object is possible, removing the risk of injury or illness from contact with the sharp object. Furthermore, the need for repeat counts is avoided. At the conclusion of the operation, if the counts are all correct, the lower chamber 235 is simply uncoupled from the imaging unit comprising the camera 215 and case 217. The lower chamber 235 containing all of the counted needles 205 and scalpel blades 210 is simply removed and incinerated in a manner similar to all of the other sharp containers present in the institution.

Figure 2B:
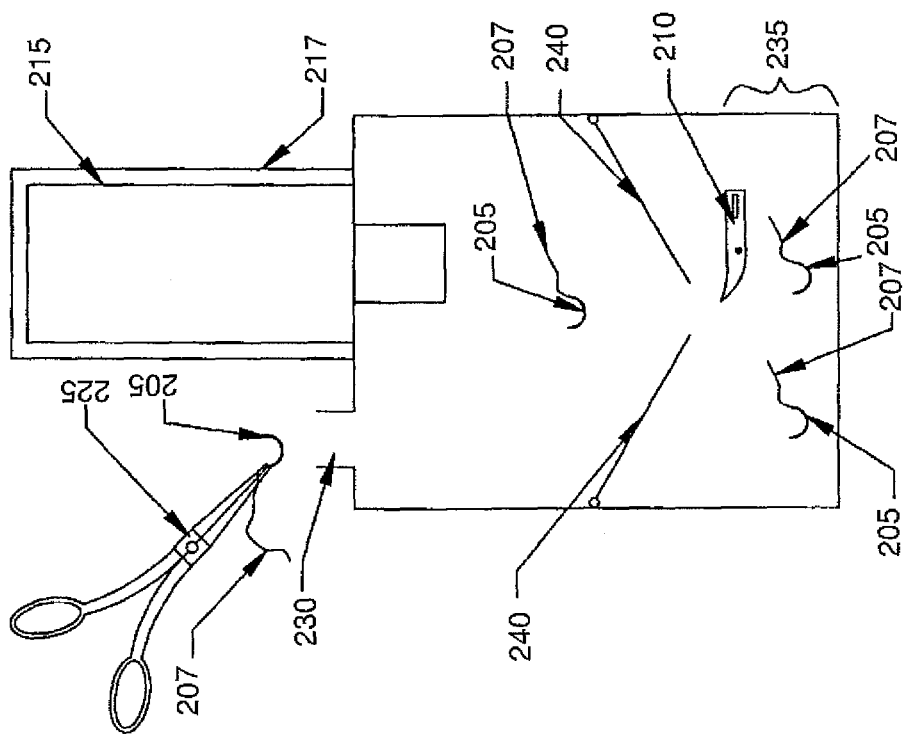
FIGS. 2B and 2C are schematics of additional embodiments of a container for identification and disposal of a surgical sharp object, according to embodiments of the invention.
Figure 2C:
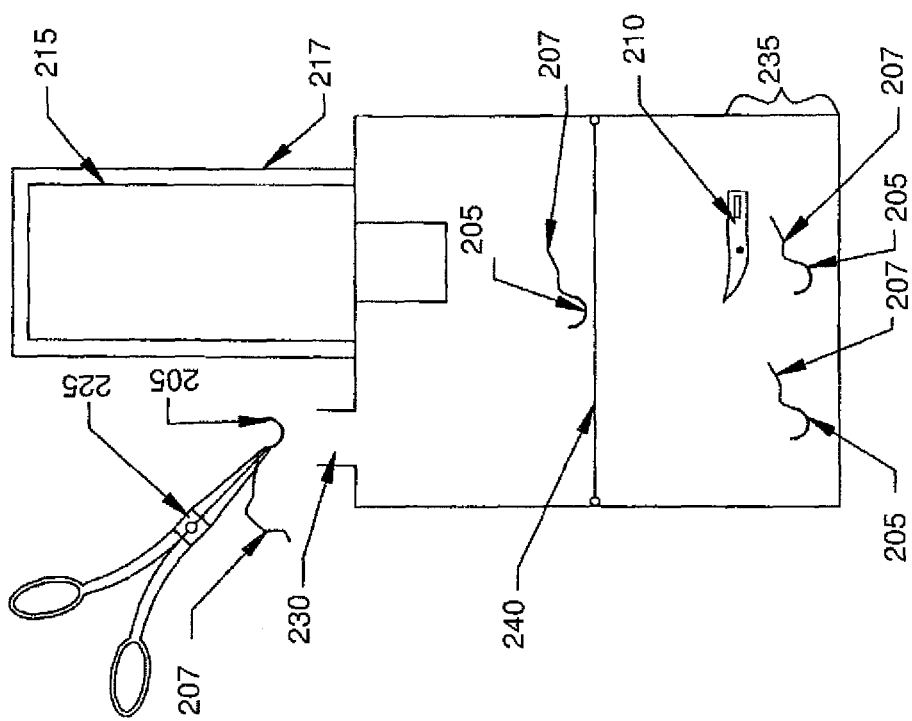

FIGS. 2B and C show another embodiment of the device for identifying and disposal of a surgical sharp object. In the embodiment shown in these figures, after the detection of the sharp object, the object is mechanically isolated from any additional added sharp objects. The container may include any convenient mechanical isolation mechanism, such as a platform which opens like a trap door. In FIG. 2B, camera 215 within the sterile case 217 detects the needle 205 or scalpel blade 210 dropped into the chute 230 after it is released from needle holder 225 and lands on the horizontal platform 240. The sharp object is then identified and counted, and the system introduces this information into a database which contains a record of the number and type of sharp objects counted into the operation. After the surgical sharp object (e.g., needle) is identified, the horizontal platform 240 opens like a trap door to allow the counted needle 205 to fall by gravity into the lower chamber 235 of the container, e.g., as depicted in FIG. 2C. The physical separation of the counted item from the image data acquisition region of the container by the horizontal platform 240 facilitates the detection and counting of the next item. FIG. 2C depicts the open trap door through which the counted item drops into lower chamber 235. As with the container shown in FIG. 2A, lower chamber 235 will be separated from the remainder of the container and discarded at the end of the operation.

Figure 2D:
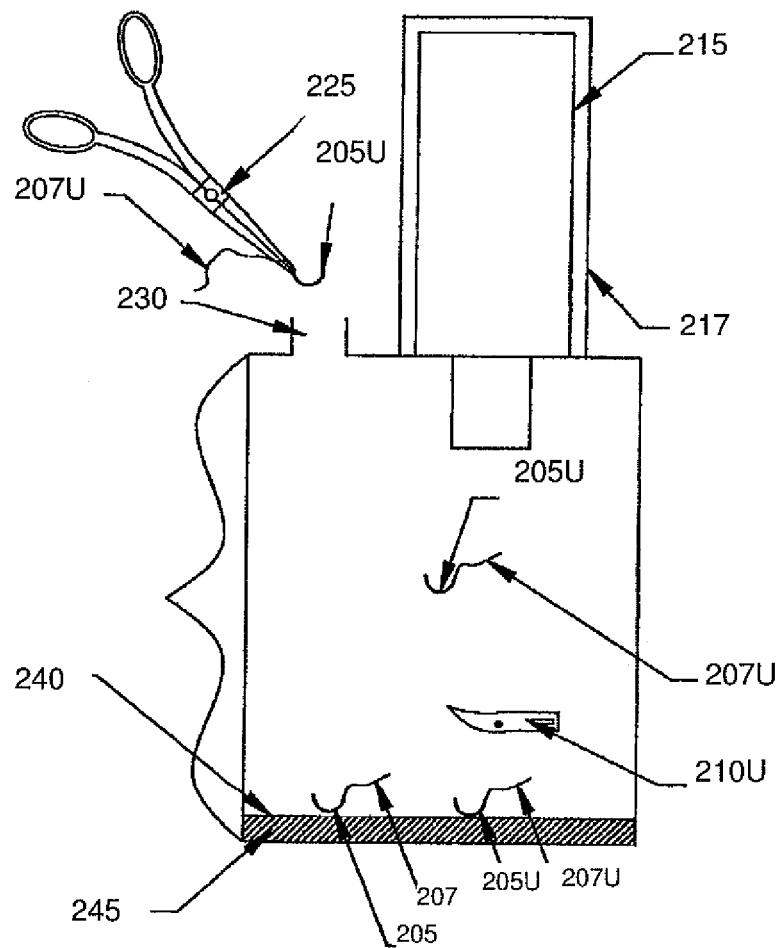
FIG. 2D is a schematic of another embodiment of a container for identification and disposal of a surgical sharp object, according to an embodiment of the invention.

In FIG. 2D, an "uncounted" needle 205U and suture remnant 207U or other sharp object such as a scalpel 210U is dropped from the needle holder 225 through the chute 230 onto the horizontal platform 240 at the bottom of the disposal container. In contrast to earlier embodiments, the as-yet uncounted needle 205U falls onto the platform 240, which can incorporate a magnet 245 or lie just above such a magnet 245, which limits motion of the counted items. In some embodiments, the platform can also include a surface that limits movement of the counted items, e.g., a surface covered with an adhesive material. The as-yet uncounted needle 205U or scalpel blade 210U lies on the platform 240 among previously counted sharp surgical objects (e.g, needle 205). In this embodiment, the automated shape recognition system is configured to count only the new addition (e.g., needle 205U) present in the camera field of view. The system can be configured to count only the newly discarded objects, making the mechanical separation discussed in the embodiments of FIGS. 2B and 2C unnecessary. The system is configured to provide an ongoing running total of various needles 205 and other sharp objects, such as scalpel blades 210. The automated shape recognition system may be configured to "correct" for errors such as, but not limited to, needles or scalpel blades that overlie each other or are crossed, bent needles, needles in close proximity to other needles or sharp objects, etc., as discussed further below.

Components of the system can also include one or more mounting devices for the imaging devices; one or more light sources; one or more containers for identification and disposal of a surgical sharp object; one or more display units; devices for the input of data (e.g., a keyboard); speech recognition capability or devices; input/output hardware or communication links with other components of a system to report results (e.g., a display unit, or automated speech confirmation of a counted or identified item); one or more devices or features to notify operating room personnel that an item is missing or unaccounted for (e.g., an auditory or visual alarm, or automated speech confirmation of a counted or identified item); one or more devices to notify operating room personnel that an item has been counted or identified (e.g., a change in color of a photochromic dye label); a computer readable storage medium; and a CPU (Central Processing Unit) for integrating the components of the system.

The subject systems can be used for automated identification and tracking of surgical sharp objects, instruments, and sponges during a surgical procedure. The functions of the subject surgical item identification and tracking system can include, but are not limited to: sensing, identifying, tracking, marking, managing, monitoring, controlling, checking, dating, timing, billing, inventory control, medical and medicolegal record keeping, and comparing with protocol.

The term "system" can include the hardware means, software means, and data storage means used to analyze the information of the present invention. Systems may include a central processing unit (CPU), input means, output means, and data storage means, etc. Any convenient computer-based system may be employed in the present invention.

In addition to, or in some cases alternatively, the system may include a number of additional functionalities beyond the automated shape recognition of sharp objects, e.g., as described above. These additional functionalities may include identification (and in some instances tracking) of surgical items beyond surgical sharp objects, such as instruments and sponges. Such additional functionalities may employ the use of unique identifiers, etc. Aspects of these additional system functionalities (which may or may not be present in a given system) are now described in greater detail.

Unique Identifiers

Additional components of the intra-operative identification and tracking systems of the invention can include one or more detectors configured to recognize a unique identifier label on a surgical item (e.g., a surgical instrument, surgical sponge or even a surgical sharp object) and a unique identifier recognition module configured to identify a surgical item by sensing or detecting a unique identifier present on the surgical item. As such, the system may be configured to employ labeled surgical items. The labeled surgical items can include a variety of different types of labeling, including but not limited to: optical labeling, microdots, ultrasound or acoustic labeling, microscopic labeling, DNA labeling, nanotechnological labeling, electro magnetic identification (EMID) labeling, conductive labeling, inductive labeling, magnetic or electromagnetic labeling, magnetomechanical markers, radiofrequency (RFID) labeling, resonant markers, capacitive coupling, macroscopic or microscopic 1D or 2D barcodes, microchips, photochromic dyes, piezochromic dye polymers, radiopaque labels, luminescent or fluorescent labels, radioactive labels, etc.

The identifier labels can be passive or active, in that they can be identifiers that are read by a detector (e.g., where the label is a barcode and the detector is a optical barcode reader), or they can be labels (i.e., identifiers) that actively transmit a signal (e.g., where the label is a transponder and the detector is a receiver configured to receive a signal emitted by the transponder). The label can be added onto a surgical item by any suitable means, such as etching, laser etching, machining, adhesive, etc., or it can be a label applied to a tag which then can be attached to a surgical item through adhesive or any other suitable means. Alternatively, the label or identifier can be incorporated into the item (e.g., an EMID label woven or otherwise incorporated into the fabric of a sponge). In some embodiments, the labels or identifiers retain their function when autoclaved or sterilized. In some embodiments, the labels or identifiers can be enclosed in a covering (e.g., a plastic covering) which allows them to retain their function when autoclaved or sterilized. The labels can be added to a surgical item at any time, e.g., during manufacturing, or in the operating room, etc.

Additionally, in some embodiments, the label can include an element which changes once detected. For example, the label may be a photochromic dye which undergoes a reversible photochemical reaction where an absorption band in the visible part of the electromagnetic spectrum changes dramatically in strength or wavelength, resulting in a visible change in color to the observer. Over time the photochromic dye can return to the original color, which allows recounting or rescanning of the surgical item. An element of a label which includes a visible change can assist operating room personnel in verifying that an item has been counted.

Different labels can be chosen for each individual surgical item, such as sponges, sharp objects or instruments. For example, an EMID tag may be used with a sponge and a microdot used with a hemostat. Factors that may be considered in the selection of a suitable label for each surgical item can include whether or not a suitable label already exists, e.g., a barcode on a pre-packaged set of needles. Other factors can include distance at which a label can be read, whether or not the label needs line-of-sight to be read, orientation requirements, size of the label or the surgical item, lighting requirements for detecting or reading the label, ability to be autoclaved, and ease of integration with the other elements of the system, etc. In addition, each member of the operating room staff can also have individual identifying labels, e.g., barcodes, that can be used to identify the personnel present in the room for a surgical procedure, as well as provide a method for authorization (e.g., an electronic "signature") for a instrument count, for example. In some embodiments, these personal identifiers can be used to assign responsibility for any individually identified or tracked surgical item. For example, if a surgical sharp object such as a 4-0 Prolene™ needle is dropped into a disposal container, the system can prompt the operating room staff (e.g., scrub nurse) who can agree or disagree with the identification, and confirm with his/her personal time stamped signature. Similarly, a dropped needle can be placed in a disposal container by the circulating nurse, who can confirm the identification of the discarded needle with his/her personal time-stamped signature. In some embodiments, the use of these personal identifiers allows the real-time assignment of responsibility for an identified or counted surgical item at any time during a surgical procedure. In some embodiments, the use of these personal identifiers can be used for the real-time assignment of responsibility for all identified or counted surgical items during a surgical procedure. The identifiers can be present in any convenient location, such as on a badge, or ID card, or bracelet, for example.

A given label can include any desired information about the items with which it is associated, including type, model, size, composition (e.g., cotton or synthetic in the case of a surgical sponge), manufacturer, date of manufacture, cost of the item, etc., in addition to providing unique identifying information for that item. For example, if there are five hemostats of similar type being used for a surgical procedure, each hemostat can have, in addition to information indicating the type of surgical instrument, etc., unique identifying information such that each of the five hemostats can be individually identified and tracked. Unique identifying information can include, but is not limited to, a unique string of numbers and/or letters, or a particular frequency, and can be used in combination with information about that particular item (e.g., the type or model). In some embodiments, a surgical item can have two or more labels, and in some embodiments a surgical item can have two or more different types of labels (e.g., a barcode and a microdot label). In some embodiments, a surgical item can have more than one label, e.g., a manufacturer-applied label and a label applied by the hospital, or even a label applied for a particular procedure.

It should be understood that the terms "identifier", "label", "tag" and "marker" are used interchangeably. Accordingly, depending on the properties of the label, the label can be used to indicate one or more of: (a) the presence of the label (and therefore the presence of the surgical item to which the label is attached); (b) the identity of the label (and therefore that of the surgical item to which it is attached); and (c) the location of the label (e.g., on the operating table or in a disposable sharp objects container). In some embodiments, the location of the label can further indicate the precise position of a label with respect to predetermined co-ordinates (and hence that of the surgical item to which it is attached). The label can also in some embodiments provide information which can be used for a system such as an inventory or billing system.

In one embodiment, surgical items can have a passive data tag, such as an EMID tag, which employs small amounts of very high-permeability magnetic material, with an alternating magnetic field for interrogation or detection. Since the magnetic material can be in the form of a thin foil, wire or film, it can be bonded directly to paper or plastic to form self-supporting tags. Further details of such labels, as well as the detectors that can adapted for use with the present methods and systems, can be found in U.S. Pat. Nos. 6,371,379, 6,230,972, and 6,054,924, the disclosures of which are herein incorporated by reference. In some embodiments, one or more of the magnetic materials on the tag is divided into distinct zones such that the zones and their relative positions can represent information or a code which is readable magnetically by passing the tag through a magnetic field which has a relatively small region of zero magnetic field (a magnetic null) contiguous with regions where the magnetic field is sufficient to saturate the magnetic material, the tag being moved through the magnetic field and its magnetic response being detected as it traverses the magnetic null. The magnets can be a permanent magnet or an electromagnet.

Magnetic labeling techniques can also include magnetostriction, programmable magnetic resonance (PMR) which employs a magnetostrictive resonator element or nonmagnetostrictive (insensitive to strain) magnetic material. Further details of labels or tags as well as the detectors that can be used in the present methods and systems can be found in U.S. Pat. No. 5,456,718, the disclosure of which is herein incorporated by reference.

FIGS. 10A-10D show other embodiments of labels that can be employed with a surgical item, such as a sponge, instrument or surgical sharp object, such as needle or scalpel. In FIG. 10A, the information is repetitively encoded as a unique microscopic serial number assigned to that particular unique surgical item, represented as a microscopic dot 1005 roughly the size of a grain of sand. Commercially available for identification purposes on casino chips since the 1990's, the application of such labels 1005 to surgical items permits the identification of each unique surgical item, such as sponge, instrument or sharp object. The application of the microscopic label 1005 can be performed by a spray adhesive type application of multiple, up to thousands, of identical labels 1005, or the multiple labels 1005 can be woven as a thread into the fabric of the a sponge. The label 1005 depicted in FIG. 10A is a number such as a unique serial number 1010 which can be read by a still camera, video camera, digital microscope, DNA-based code reader or other software based reader, etc., capable of reading the actual serial number or other identifier assigned to the surgical item of interest. The detected label 1005 containing the serial number 1010 is microscopic in this depiction. The reader or camera may or may not be used with magnification via a microscope lens 1015, depending on the capabilities of the detector. FIG. 10B depicts in greater detail an embodiment of a microscopic label 1005 in which the identifier is 1D barcode 1020. Again, the reader may or may not use magnification via lens 1015 to facilitate reading the unique microscopic 1D barcode 1020. In FIG. 10C, the unique identifier is a microscopic 2D barcode 1025, identified via lens 1015. As shown in FIG. 10D, a digital microscope 1030 can be used to digitally magnify and detect the identifiers 1005.

Dectectors

Detectors for detecting labeled surgical items can include but, are not limited to, detectors for reading labels, including conventional scanners which are adapted to sense the presence of conventional integrated circuit (IC) transponders on or within articles; devices that establish electromagnetic fields and sense the presence of a conducting element in the fields, such as dipole wire elements, microchips, microtransponders, microtransmitters or threads in the articles (which may be encoded if desired); sensors for detecting electro magnetic identification (EMID) labels; radiofrequency (RFID) label detectors; radiation detectors adapted to sense radioactive tracers in the articles; receivers adapted to sense signals from transmitters in the articles; sensors adapted to sense radiopaque handles or threads in the articles; photoelectric or optical sensors adapted to read macroscopic or microscopic 1D or 2D barcodes or other codes in or on the articles; optical character recognition detectors; MRI detectors which sense MRI active polymers or other materials; magnetic or electromagnetic label detectors, magnetomechanical marker detectors; ultrasound or acoustic readers; DNA label readers; nanotechnological label readers; inductive label readers, conductive label readers; resonant marker detectors; capacitive coupling detectors and sensors; photochromic dye readers; color sensors; video cameras; transponders adapted to sense the presence of passive electronic ID radio tags; laser scanners; cameras; thermal detectors; luminescence detectors; infrared detectors; piezoelectric detectors; fluoroscopic detectors; electronic article surveillance (EAS) system detectors, such as magneto-harmonic, acousto-magnetic or magnetostrictive and microwave detectors, any other suitable detector for detecting surgical items. In some embodiments, a conductive detector that can detect a surgical item by physically touching a label directly, or by physically touching a surgical item with an attached label can be used to retrieve the unique identifier for the surgical item. In some embodiments, a conductive detector can have a low power output, and can detect the presence of a label (e.g. an electrical binary code label, or integrated circuit label). In some embodiments, a circuit can be formed by the connection of electronic labels on multiple surgical items (e.g., instruments) where each surgical item has an individual unique label. By physically touching one instrument or label on an instrument in the circuit, the conductive detector can simultaneously or nearly simultaneously detect all of the unique identifiers on all of the surgical items in the circuit. In this embodiment, the circuit formed by multiple surgical items (e.g., conductive metal instruments, or conductive metal added to connect instruments to complete the circuit) facilities rapid identification. In some embodiments, an inductive detector can be used which can detect a surgical item or multiple surgical items by sufficient physical proximity to retrieve the unique identifier, which may or may not be connected by a conductive circuit (e.g., conductive metal instruments, or conductive metal added to connect instruments to complete the circuit). In some embodiments, an inductive detector can also simultaneously or nearly simultaneously detect all of the unique identifiers on all of the surgical items, when the surgical items are in sufficiently close proximity to allow inductive detection. In some embodiments, the detector can be an imaging device, which can be used to obtain image data of, for example, a surgical sharp object using a process of automated shape recognition, as discussed above.

The detectors can be passive or active, in that a detector can read a label (e.g., barcode, electrical binary code label, or integrated circuit label), or a detector can actively transmit a signal to a label and check for a response (e.g., transponder).

The detector can also be configured to detect a label characteristic, such as visual characteristic. In some embodiments, the detector can activate a change in a label characteristic (e.g., cause a change in color of a photochromic dye) on a surgical item, which indicates that a surgical item has been counted. As indicated above, surgical sharp object disposal containers may include one or more suitable light sources, which can be specialized light sources such as a light-emitting diode (LED) illuminators, fluorescent or halogen lamps, etc. The lighting can be used to illuminate the surgical sharp object to be imaged, and can also be used to highlight features of interest and obscure or minimize the appearance of features that are not of interest (such as shadows or reflections). The lighting can be located in any suitable location, including on or near the camera, or on or under a surface or platform where the surgical item to be imaged is placed, including lighting that is "front-lit", "back-lit", direct on-axis lighting (DOAL), off-axis lighting, multi-axis lighting, etc.

The detector for detecting the labeled surgical items can be hand-held, or it can be mounted, for example, such that it is in a stable position relative to a table such as a sterile back table or a "mayo stand". Alternatively, the detector can be mounted from a ceiling or wall fixture overhead, for example, such that it is in a stable position relative to an operating room table or a sterile back table. In some embodiments, the mounting apparatus or hardware for securing the detector can be adjustable, such that the distance from the detector or viewing angle of the detector relative to the surgical items being detected can be adjusted. In other embodiments, the mounting apparatus for securing the detector is in motion, such that the detector can continuously scan the items on a sterile back table or in the operating field. In some embodiments, a detector can be capable of being hand-held or placed on a stand, for example, a detector can be held by a circulating nurse to register one or more surgical items, and then can be placed on a mounting apparatus on a sterile back table, so that the detector can register items placed on the sterile back table. The detectors can therefore be positioned to image surgical sharp objects, surgical instruments or surgical sponges that have been placed onto a sterile table; e.g., a sterile back table. In some embodiments, the detector can be part of a container, such as a surgical sharp objects container configured for disposal of the sharps, discussed further above.

Factors that may be considered in the type, number, and placement of detectors in the operating room can include the distance at which a label can be read, whether or not the label needs line-of-sight to be read, lighting requirements for detecting or reading the label, orientation requirements, size of labels and/or detectors, and ease of integration with the other elements of the system. Detectors can also incorporate or be used with a magnifying lens, and in some embodiments, the detector can be an optical or digital microscope.

The detector can be powered as desired, e.g., with a battery, with building electricity or any other suitable power source. The detector can transmit data using any convenient protocol, such as via a cable connection via a wireless communication protocol. The detector can be sterile or non-sterile, and in some instances can change from one status to another. For example, a sterile covering may be placed over a previously non-sterile detector, as desired.

Multiple different detectors can be used in multiple locations around the operating room. More than one detector can be used in one location (e.g., one or more detectors can be mounted over the operating table), and in some embodiments, more than one type of detector can be used in one location (e.g., a barcode reader and a EMID tag reader may be mounted on a sterile back table). In other embodiments, a single detector can have more than one capability (e.g., a single hand-held detector can be capable of reading barcodes and microdots).

Depending on the properties of the device, the detector can perform a number of different functions, such as detecting the presence of a label (and therefore the presence of the surgical item to which the label is attached); identifying the label (and therefore the identity of the surgical item to which it is attached); or determining the location of the label (e.g., on the sterile back table or in a surgical sharp objects disposal container). In some embodiments, by detecting the location of the label, the precise position of the label can be determined with respect to predetermined co-ordinates (and hence that of the surgical item to which it is attached). Detection of the label can also include automatic entry of the information into the system, and can include display of the information on a visual display unit, e.g., an LCD or plasma monitor, of the system. Detection of the label can also, in some embodiments, be used to provide information which can be used for a system such as an inventory or billing system. As used herein, the terms "to sense", "to detect", "to scan", "to read", "to identify", and "to register" are used to indicate the process of determining the presence of a label, the information carried by a label, the location of the label, the time the label is read, etc., as described above. In some embodiments, the detector can identify a surgical item (e.g., forceps or surgical needle) without the need for a label by using automated shape recognition, e.g., as discussed further above.

Detection of an item can be performed when the item of interest is moving (such that the item is dynamically detected) or when the item of interest is stationary (such that the item is statically detected). For example, an item may be dynamically detected by placing the item within the range of a detector, such as placing the item beneath a detector or moving an item past a detector, or vice versa (such as where a hand-held detector is moved past the item). For static detection, detection can be performed while the item of interest is stationary, e.g., on a sterile back table. In some embodiments, if the detector is part of a device, such as a container for identification and disposal of a surgical sharp object (such as described above), the item can be scanned as it is dropped into a container, e.g., a disposable sharps container. In other embodiments, a fixed scanning device can have a slot through which objects may be passed through for pre-operative or post-operative scanning. Individual objects, such as packaged sutures or scalpel blades, or similarly, groups of objects, such as lap pads or sponges, can be fixed to a reusable or disposable holder and scanned for pre-operative counting. The same or a different reusable or disposable holder for used lap pads or sponges can also be used for post-operative scanning. In some embodiments, a scale can be included with a scanning device (e.g., for scanning sponges) for determining the weight of blood or other fluid contained within the sponges and lap pads after the surgical procedure.

In one embodiment, such as when EMID tags are employed, the detectors can sense the presence of a magnetic tag, by passing the tag through a magnetic field which has a relatively small region of zero magnetic field (a magnetic null) contiguous with regions where the magnetic field is sufficient to saturate the magnetic material, the tag being moved through the magnetic field and its magnetic response being detected as it traverses the magnetic null. Further details of labels or tags as well as the detectors that can be adapted for use with the present methods and system can be found in U.S. Pat. Nos. 6,371,379, 6,230,972, and 6,054,924, the disclosures of which are herein incorporated by reference.

Labels and detectors, e.g., as described above, may be employed in the detection and tracking of a variety of different surgical items, including surgical sharp objects (i.e., sharps), instruments and sponges. Detection and tracking of each of these types of surgical items is now reviewed in greater detail below.

Sharps Detection and Tracking

Surgical sharp objects, such as scalpels, blades, or needles, can be labeled, detected, and tracked using any of the one or more systems and methods disclosed above. In one embodiment, the "inbound", or initial counting of a surgical sharp object can be performed by reading a barcode on the packaging of a needle. The tracking of surgical sharp objects during a surgical procedure, as well as the "outbound", or final count before wound closure, can be performed via a shape recognition protocol, e.g., as described above, either in conjunction with or instead of a label identification protocol. As such, methods of tracking surgical sharp objects can include imaging a surgical sharp object to obtain image data, and then identifying the surgical sharp object using the image data by automated shape recognition, as described above. In some embodiments, imaging of the surgical sharp object is performed by a container configured for disposal of the surgical sharp object.

In addition to surgical sharp objects, various sizes and/or types of screws, bolts, plates and other hardware such as those used in orthopedic surgery or neurosurgery can be labeled, detected and tracked using any one or more methods disclosed above, including automated shape recognition.

Figure 3A:
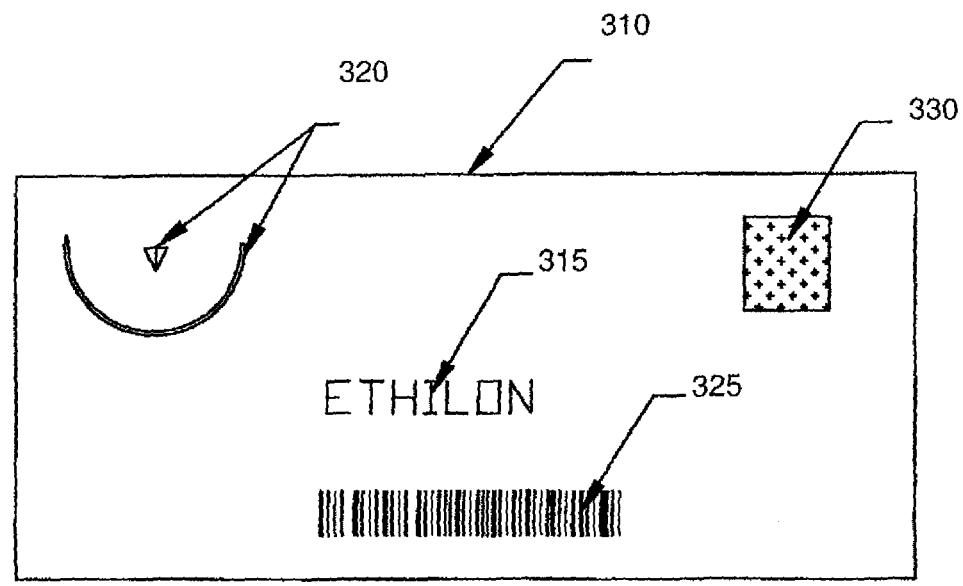
FIGS. 3A-C are schematics of various aspects of a needle or other sharp object that can be identified by recognition of a unique identifier in one embodiment of the invention.
Figure 3B:
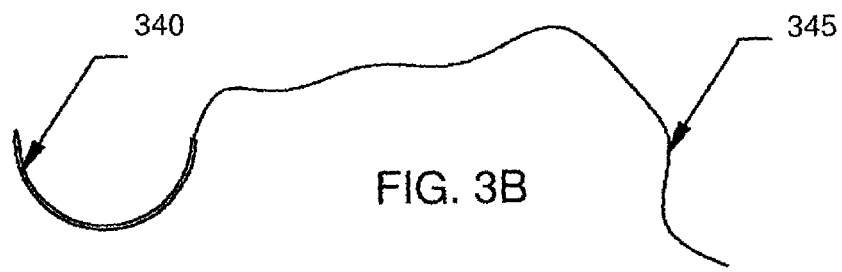
Figure 3C:
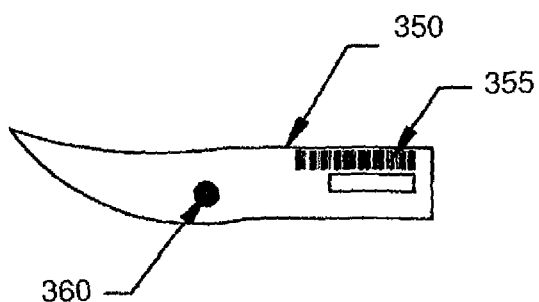

FIGS. 3A-C depict exemplary surgical sharp objects that include labels that can be employed for the initial count before the operation begins. Additional items that are required by the surgeon as the operation progresses can be counted in a similar manner as needed. FIG. 3A depicts a pre-packaged container 310 in which the needle and suture to be added to a surgical field in a sterile manner is delivered by the manufacturer. The pre-packaged container 310 lists the name of the suture and needle type, pre-printed information 315 such as the manufacturer (e.g., Ethicon™) and other information of value to the hospital and staff, such as lot number. The pre-printed information can be used for "inbound" counting; e.g., by a barcode reader. Pertinent to counting the item optically is an actual size picture 320 or diagram of the needle and/or a 1D barcode 325 or 2D barcode 330 with an identifying code for that specific needle type and suture. FIG. 3B depicts a surgical needle 340 and suture 345 after the packaging has been discarded. In some embodiments, the exposed needle 340 and suture 345 can also be counted by automated shape recognition, for example, using automated shape recognition equipment, in cases where the count was not performed already on the packaging 310 with an identifying picture or diagram 320, 1D barcode 325 or 2D barcode 330, for example as shown in FIG. 3A. Some needles 340 used in surgery are designed for repeat uses in which different lengths of suture are added to the eye of the needle. Automated shape recognition of the individual needle is particularly suited to identifying these needles in cases where the packaging does not convey identifying information in barcode format. For example, the surgical sharp object (e.g., needle) can be imaged to obtain image data, and then identified using automated shape recognition. FIG. 3C depicts a disposable scalpel blade 350 shown already removed from its packaging (and thus removed from any associated barcode information). However, in this example, the blade itself has a 1D barcode 355 and/or 2D barcode 360 laser etched into the steel of the blade or onto a label then applied to the blade, which facilitates the quick detection of the sharp object, e.g., with a unique identifier recognition module. If the barcoding is absent, automated shape recognition of the blade itself can be used to detect, identify, and count the sharp object (e.g., scalpel blade).

FIGS. 4A and 4B show examples of hand-held scanners designed to detect the surgical sharp objects to be counted whether they are presented in their original packaging or have been removed from the packaging. FIG. 4A is a schematic of a hand-held scanner 400 (or alternatively a mounted camera) designed to detect needle and suture packaging 410 marked with 1D barcoding 425, 2D barcoding 430, pre-printed information 415, or actual size picture 420. Also shown is scalpel blade 440 marked with a 1D barcode 425 and a 2D barcode 450. The hand-held scanner 440 can be used to scan and identify the sharp objects and convey the information to be processed by the system, updating the count as the items are added to the field by the circulating staff. Alternatively, a sterile hand-held device 480 may be used by the scrub nurse to count the needle 470 already added to the field, but not yet added to the count. A sterile case 460 enclosing the hand-held scanner 400 maintains the sterility of the field. The information pertaining to the identification of the needle, aided by the additional information identifying the attached suture 475 when desired, is transmitted, e.g., wirelessly or via sterile cable or a cable also within the sterile case or sheath, to the other components of the system for data management.

Instrument Detection and Tracking

Instruments can be labeled, detected, and tracked using any of the one or more methods disclosed above. In one embodiment, the "inbound", or initial counting of a surgical instrument, tracking during a surgical procedure, and the "outbound", or final count of surgical instruments before wound closure can be performed by a unique identifier recognition module (e.g., by detection of a barcode, a RFID tag, or laser-etched tag, etc.). The methods of instrument detection can be used with reusable or disposable instruments.

By surgical instruments is meant tools or implements used during a surgical procedure or operation, including but not limited to: graspers such as forceps, needle holders, clamps, retractors, cutting devices such as scalpels, scissors, or trocars, etc., dilators, irrigation or suction devices, hemostats, etc. In some embodiments, this can include other items that are used in a surgical procedure such as syringes, red rubber catheters, suture holders, or any other item present in the surgical procedure room that has the potential to be unintentionally retained in a patient, and is therefore is included in operating room policy counting protocol.

Figure 5A:
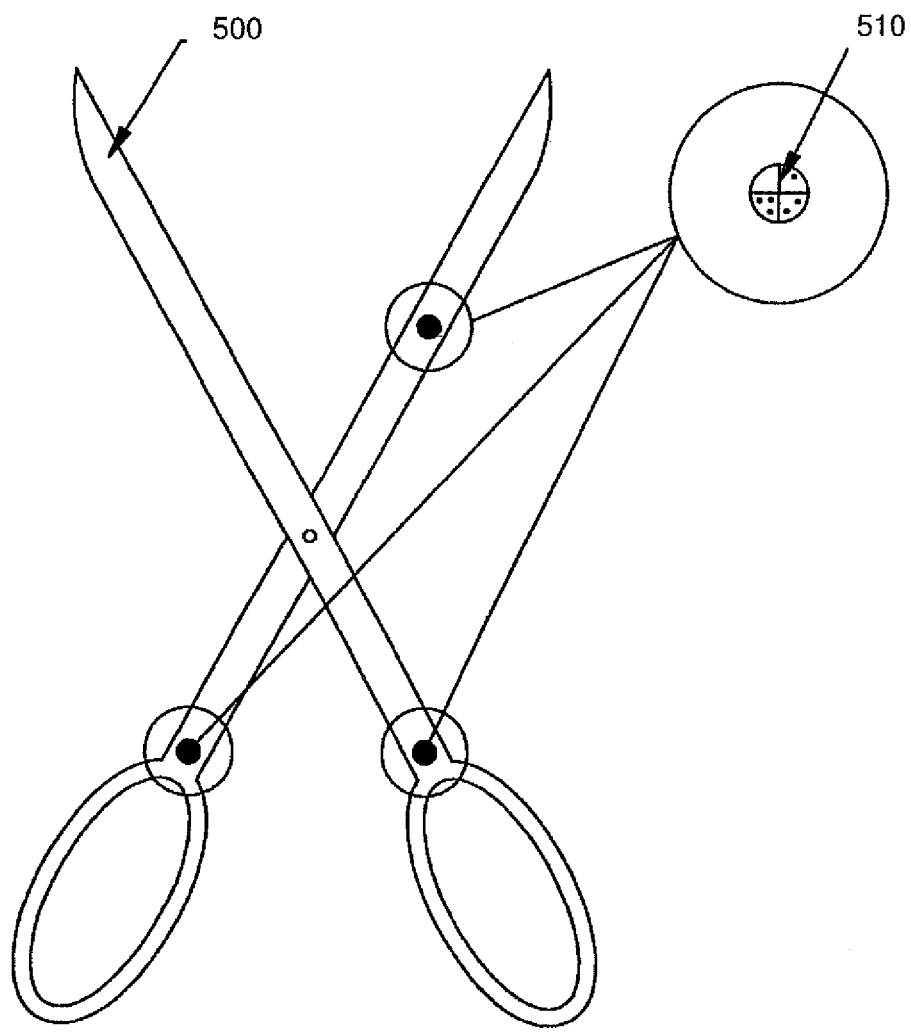
FIG. 5A provides a view of a surgical instrument with a unique identifier in the form of a 2D barcode in accordance with an embodiment of the invention.

FIG. 5A depicts an example of a metal instrument used in surgery. An instrument 500 (e.g., scissors) can be marked by either laser etching the metal of the actual instrument or by application of a laser etched label 510 to the metal of the instrument. The application of the barcode to the instrument provides for a unique identifier assigned to the individual instrument 500. Thus, when the barcode label 510 is detected, the unique identification and counting of that particular instrument 1 is accomplished. FIGS. 5B to 5E provide schematic views of various labeling possibilities for surgical instrument 500. FIG. 5B depicts a surgical instrument 500 labeled by the spray application of many multiple microscopic identifiers 520, such as commercially available "microdots" with a unique identifier such as a serial number, DNA label, or 1D or 2D barcode. FIG. 5C depicts a similar instrument 500 which has been labeled by, in this example, four small but macroscopic 2D barcodes 530 (similar to those described in greater detail below) at four locations on the particular instrument. FIG. 5D depicts a combination of possible labeling techniques in which the instrument 500 has been labeled with commercially available surgical instrument tape 540 which itself has been labeled with one or more macroscopic 2D labels 530 and/or microscopic labels 520. FIG. 5E shows yet another embodiment in which a combination of microscopic and macroscopic labels are used. In this embodiment, the scissors 500 have been labeled with threads 550 incorporating microscopic labels 520 applied to the instrument 500 along one axis and handle and additional microscopic labels 530 have been spray applied or wrapped on the other axis of the scissors 500. Alternatively, the label may be etched, including laser etching, or applied using a permanent direct product marking (DPM) process such as dot "peening" to the particular instrument, or tag attached to the instrument, needle or sponge depending on the physical characteristics of the item to be identified. In some aspects of the invention, more than one label as well as more than one type of label as in these embodiments can be used to enhance the accuracy and reliability of the methods.

Figure 6:
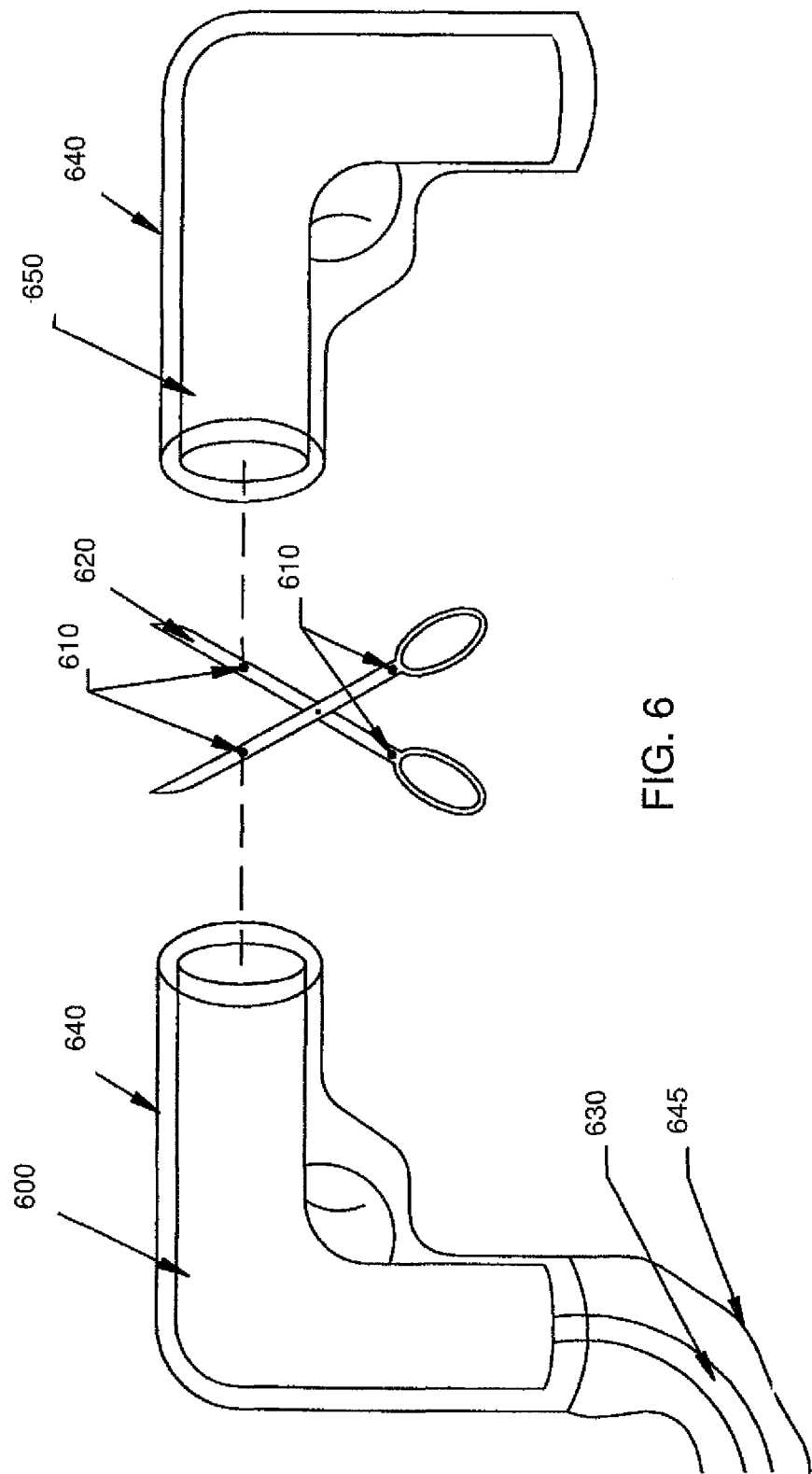
FIG. 6 provides a view of an embodiment of a unique identifier recognition system that can be used to detect a unique identifier on a surgical instrument.

A schematic view of one embodiment of the unique identifier recognition module configured to recognize an individual instrument is shown in FIG. 6. In FIG. 6, a handheld detection reader 600 is utilized to detect the unique identifier barcode label 610 applied prior to surgery to each instrument 620. The handheld reader 600 detects the label 610 and transmits the information via cable 630 to other parts of the system, e.g., a tracking module. In order to maintain the sterility of the operative field, the detection reader 600 can be enclosed in a sterile case 640 and the connecting cable 630 can be enclosed in a sterile sleeve 645. Connecting cable 630 can carry information from the detection reader 600 to a central processing unit as well as to other components of the system. In FIG. 6, the handheld detection reader 600 may be replaced by a reader 650 which is enclosed in a sterile case 640 to maintain the sterility of the operative field. The reader 650 is analogous to reader 600, except that no connecting cable is necessary because the detected information associated with the unique identification of that particular instrument 620 is transmitted to the central processing unit (CPU) using any suitable method such as e.g., BLUETOOTH, WI-FI, WI-MAX or other wireless communication protocol.

Counts can be performed with the automated embodiment prior to the initiation of the skin incision at the beginning of the operation. In addition, counts can be performed whenever desired later in the operation. The described embodiment fits well with currently accepted protocols, which require the agreement by two members of the operating room staff on the initial and final counts and any changes during the operation. Recording the accuracy of the count by time-stamping the performed counts automatically allows real-time accuracy throughout the operation. The detectors may be configured to read barcodes assigned to the pertinent personnel agreeing to the count. In such instances, by simply having the detector read the personnel code as instruments 620 are added to or removed from the field, the accuracy of the count and counters is enhanced.

Figure 7:
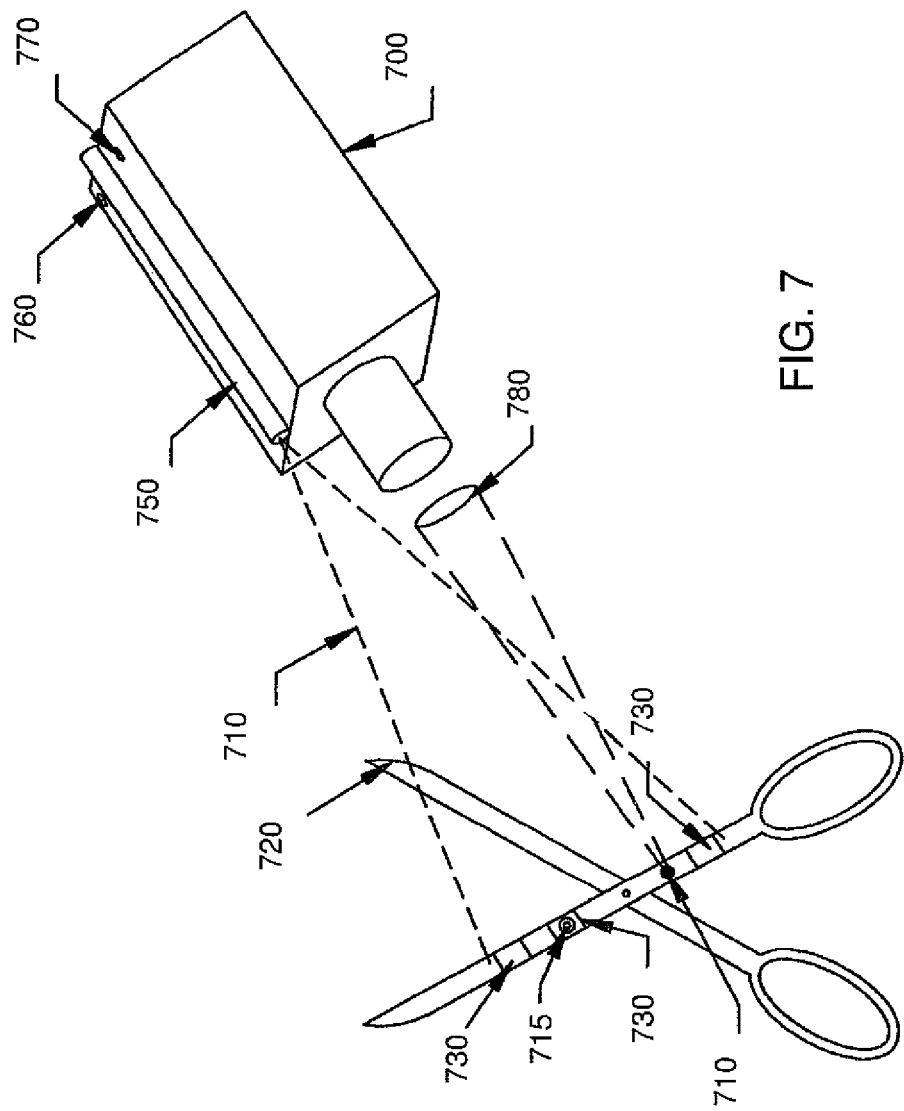
FIG. 7 provides a view of another embodiment of a unique identifier recognition system that can be used to detect a unique identifier on a surgical instrument.

An alternative embodiment of an instrument detector is shown in FIG. 7. FIG. 7 is a schematic of a surgical instrument recognition detector 700 configured to detect a unique identifier in the form of microscopic serial number 710 assigned to the unique surgical item, such as instrument 720. The schematic depicts one of the multiple possible methods which can be used to indicate to the operator the reading of the particular serial number 710 assigned in this case to instrument 720. In this depiction, there is a photochromic dye 730 associated with, e.g., overlying or adjacent to, the serial number present on microscopic label 710 or adjacent to the macroscopic label. The dye is activated by light emitted by the detector 700 to aid the detection of the identifier. Alternatively, a parallel beam of appropriate light 740 (UV or otherwise) is emitted from another source 750 incorporated into or on the detector 700 as the detector 700 simultaneously scans over the labels 715 and/or 710 thereby activating the photochromic dye. The photochromic dye within the polymer applied to the counted item, in this case an instrument 720, changes color once it has been detected indicating to the operating room personnel that the instrument has been counted. The detector 700 itself can also indicate it has read the serial number on the instrument label by emitting an audio beep from sound source 760 and/or visual indication by illuminating a light or LED indicator 770 on the detector 700. In addition, the actual name of the counted item can be displayed if desired on the main display unit to further confirm in real-time the accurate count of the instrument 720.

The use of the photochromic dye/polymer on the counted item can be useful in that it provides an additional indicator (e.g., in the form of a color change of the dye) for the operating room personnel performing the count to see. Therefore, if the scanning personnel fail to see a surgical item color change of the photochromic dye, the operator of the detector 700 immediately knows to rescan the instrument 720. Therefore, failure of the surgical item to be successfully scanned can be determined independent of the camera/reader-based system. Conversely, time is not wasted rescanning an item already indicated by the color change that it has been counted, (which can be confirmed by evaluation of the sensor system display monitor) and thus the counting is expedited and the entire process is more efficient.

Multiple different photochromic dyes are available which may permit multiple color changes for multiple scans, if desired. The time period the photochromic dye emits the light is also variable, which allows for much adjustment of the desired counting process. The photochromic dye may be applied directly to the item to be counted, can be incorporated into or onto the labeling barcode or other identifying modality or it can be applied to surgical tape which itself is then applied to the surgical item.

Other protocols for marking or identifying the item as it is counted can be used as disclosed above. Examples of such protocols include, but are not limited to, conductive detection, inductive detection, radiofrequency identification, piezochromic dye polymer changes on the counted item (touch initiated color change) and/or audio and/or visual signals on the detector itself. Conductive, radiofrequency, piezochromic and/or simple audio beeps or visible lights on the reader in addition to the real-time appearance on the display module are also possible modalities to indicate the successful reading of the identifier.

In some embodiments, the unique identifier on a surgical instrument is a conductive label (e.g. a label that can be detected through conduction, such as an electrical binary code label, or integrated circuit label) that can be detected by physically touching the label directly with an appropriate conductive detector. In other embodiments, the unique identifier can be detected by physically touching the surgical instrument with an attached label with a suitable conductive detector. In some embodiments, a conductive detector can have a low power output that can detect the presence of the label. In some embodiments, a circuit can be formed by the connection of electronic labels on multiple surgical instruments wherein each surgical instrument has a unique label. By physically touching one label (or instrument with attached label) in the circuit, the conductive detector can simultaneously detect all of the unique identifiers on all of the surgical instruments in the circuit. In this embodiment, the presence of a circuit formed by multiple surgical instruments consisting of conductive metal in contact with the unique identifiers facilitates the rapid identification of the surgical instruments in the circuit. In some embodiments, the unique identifier on a surgical instrument is an inductive label (e.g. a label that can be detected by induction) that can be detected with an appropriate inductive detector in sufficient proximity to detect the unique identifier. In some embodiments, an inductive detector can simultaneously detect one or more unique identifiers on a group of one or more surgical instruments with an appropriate inductive detector, by bringing the inductive detector in sufficient proximity to the group of instruments to detect the unique identifiers in the group of instruments.

Figure 8:
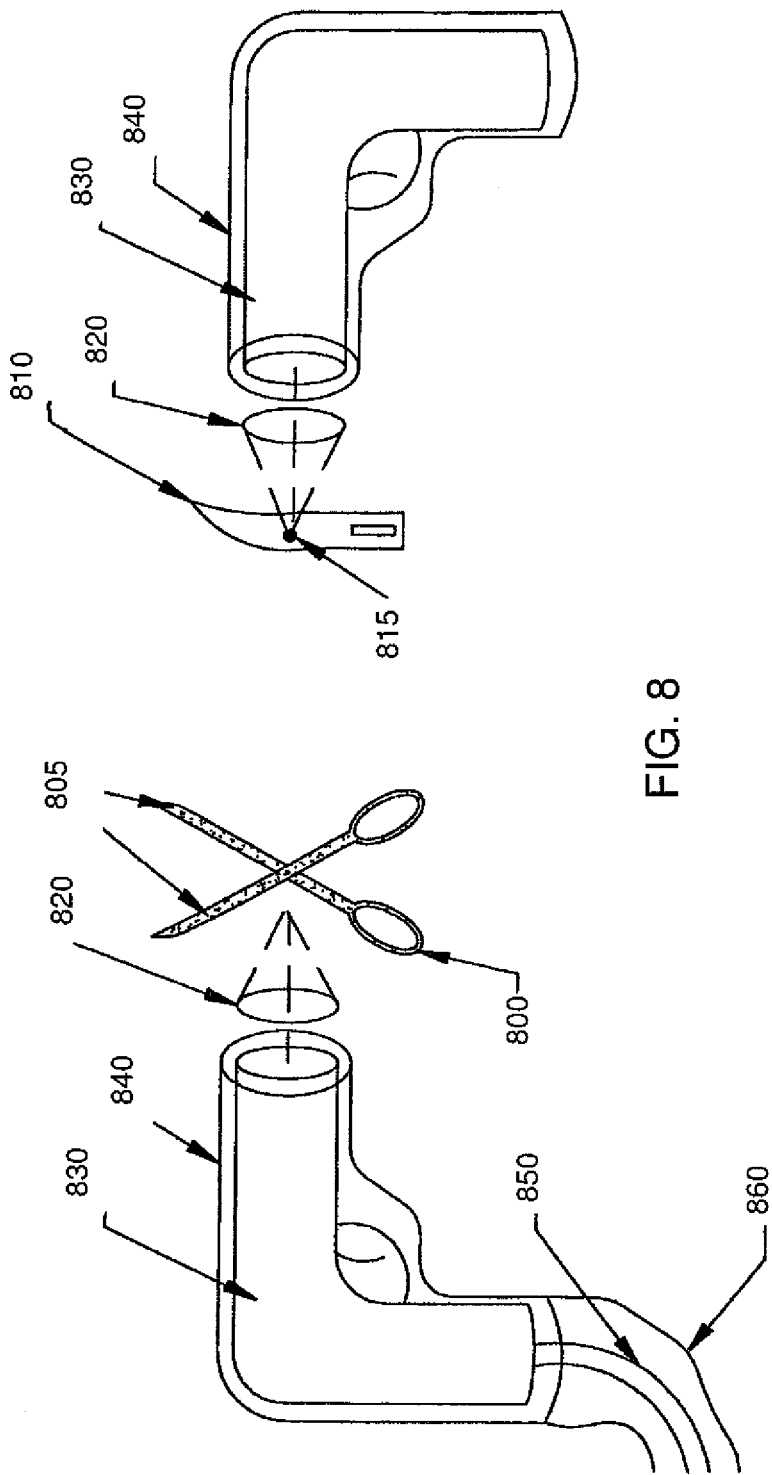
FIG. 8 provides a view of an embodiment of a unique identifier recognition system that can be used to detect a unique identifier on a surgical instrument or sharp object.

FIG. 8 is a schematic view of a unique identifier recognition module configured to recognize an individual instrument 800 or sharp object 810 by recognition of a unique identifier (805 or 815 respectively) applied to the particular surgical item. In this embodiment, identifier 805 is a unique microscopic serial number that has been assigned to the individual instrument 800 (depicted as scissors). The identifier 805 is detected via magnification through lens 820 and then the detector 830 enclosed in a sterile case 840 reads the information and relays it to the central processing unit via cable 850 encased in a sterile sleeve 860. Software incorporated into the central processing unit, such as optical character recognition programs, identifies the item read as unique. In another embodiment, a digital microscope/reader can digitally incorporate the necessary magnification to read the microscopic serial number assigned to the instrument 800. If the instrument needs to be removed from the field because of contamination or malfunction, a similar non-sterile reader and cable can be used by circulating, non-scrubbed personnel to identify and count the removed instrument 800. In this manner, tracking of that particular instrument is current, and the status of the instrument as on or off of the operative field is displayed in real-time for all operating room personnel to see. FIG. 8 similarly depicts the recognition of an individual sharp object (in this case a surgical scalpel blade 810) labeled with a unique microscopic serial number on label 815. The detector 830 enclosed within the sterile case 840 reads the serial number of label 815 magnified by lens 820 and relays it to the central processing unit via one of many available wireless transmission systems. As described above, non-sterile similar detection devices are used to detect and identify and time-stamp any sponge, instrument or sharp item removed from the field. All detectors in the operating room can be integrated into the system via wired or wireless connection to track in real-time all surgical items such as sponges, instruments and sharp objects in use for the particular operation.

Sponge Detection and Tracking

Textile-based items, such as sponges, gauze, towels, or lap pads, can also be labeled, detected, and tracked using any of the one or more methods disclosed above. In one embodiment, the "inbound", or initial counting of a sponge or lap pad, tracking during a surgical procedure, and the "outbound", or final count before wound closure can be performed by a unique identifier recognition module (e.g., by detection of a barcode attached to or embedded in a sponge; a conductive or inductive tag detected by an appropriate reader; a RFID tag; or EM barcode, etc.) In some instances, textile-based items are objects that are configured for one time use, such that they are to be disposed of following their use in a given surgical procedure, and in some embodiments, textile-based items are reusable. In some embodiments, the pre- and post-operative weight measurement of discarded sponges can also be obtained, which could provide an estimate of the amount of fluid or blood loss from a patient.

Figure 9A:
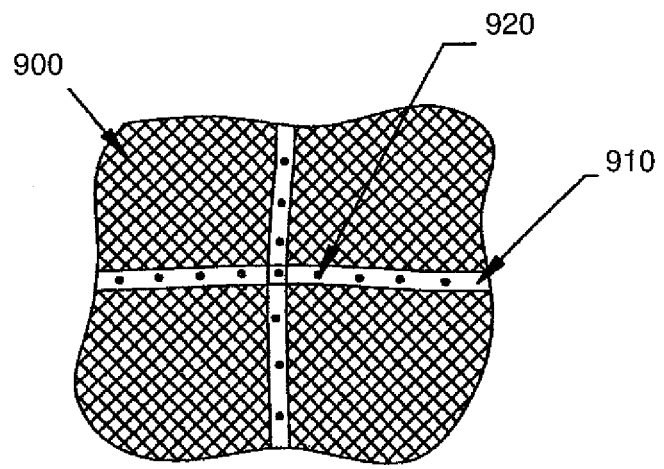
FIGS. 9A-9C are schematics of surgical sponges with unique identifiers, in accordance with embodiments of the invention.
Figure 9B:
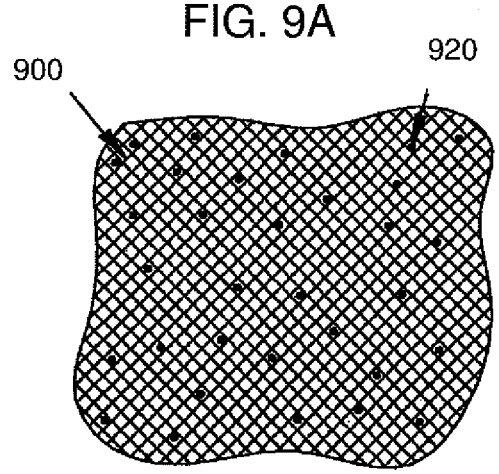
Figure 9C:
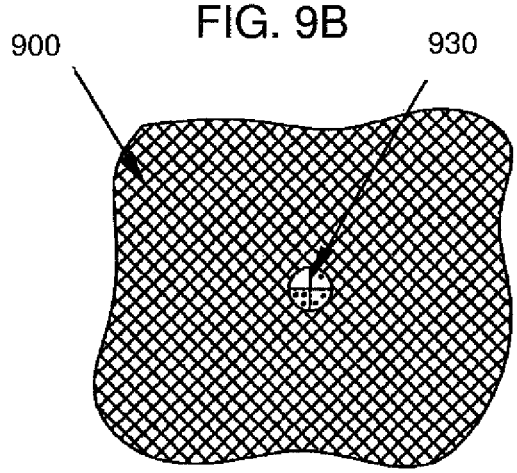

FIGS. 9A-C depict a woven sponge 900 or other textile-based object often used in surgery. In FIG. 9A, the sponge 900 is marked by weaving or otherwise incorporating one or more uniquely microscopically labeled threads 910, which could be a unique identifier such as microscopic or macroscopic serial number or barcode, 1D barcoding, 2D barcoding, 3D visualization based, DNA labeled, nano particle labeled, radiofrequency labeling, ultrasonic, conductive, or electromagnetic labels, etc., as desired. Currently used operating room sponges similarly have a woven, radio-opaque, such as barium-based, identifier for identifying the sponge should it be retained in a body cavity. In some embodiments, one or more labels can be used on the same sponge, including, for example, the currently used radio-opaque markers. The purpose of the microscopically labeled thread 910 in the described methods is to identify the sponge 900 and prevent the retention of the foreign body sponge 900. In this embodiment, identification of the unique sponge is achieved by reading a microscopic label 920 incorporated multiple times into the thread 910 woven one or more times into the woven sponge 900. In FIG. 9B, the identical microscopic identifiers 920 are spray applied to the sponge itself, rather than incorporated into a single thread. The labels, whether microscopic or macroscopic, single or multiple, are identical for each individual counted item and label each item as unique. In FIG. 9C, a macroscopic 2D barcode label 930 has been attached in one or multiple locations on the sponge 900. The application of the macroscopic barcode label 930 to the counted item provides unique identifying information assigned to the sponge 900. Thus, when the barcode label 930 is detected the unique identifying information and counting of that particular sponge 900 is accomplished.

In some embodiments, the unique identifier on a surgical sponge is a conductive label (e.g. a label that can be detected through conduction, such as an electrical binary code label, or integrated circuit label) that can be detected by physically touching the label directly with an appropriate conductive detector. In other embodiments, the unique identifier can be detected by physically touching the surgical sponge with an attached label with a suitable conductive detector. In some embodiments, a conductive detector can have a low power output that can detect the presence of the label. In some embodiments, a circuit can be formed by the connection of electronic labels on multiple surgical sponges wherein each surgical sponge has a unique label (e.g., with a metallic thread, or other suitable connection). By physically touching one label (or sponge with attached label) in the circuit, the conductive detector can simultaneously detect all of the unique identifiers on all of the surgical sponges in the circuit. In this embodiment, the presence of a circuit formed by multiple surgical sponges connected through conduction facilities rapid identification of all of the surgical sponges in the circuit. In some embodiments, the unique identifier on a surgical sponge is an inductive label (e.g. a label that can be detected by induction) that can be detected with an appropriate inductive detector in sufficient proximity to detect the unique identifier. In some embodiments, an inductive detector can simultaneously detect one or more unique identifiers on a group of one or more surgical sponges with an appropriate inductive detector, by bringing the inductive detector in sufficient proximity to the group of sponges to detect the unique identifiers in the group of sponges.

Figure 11:
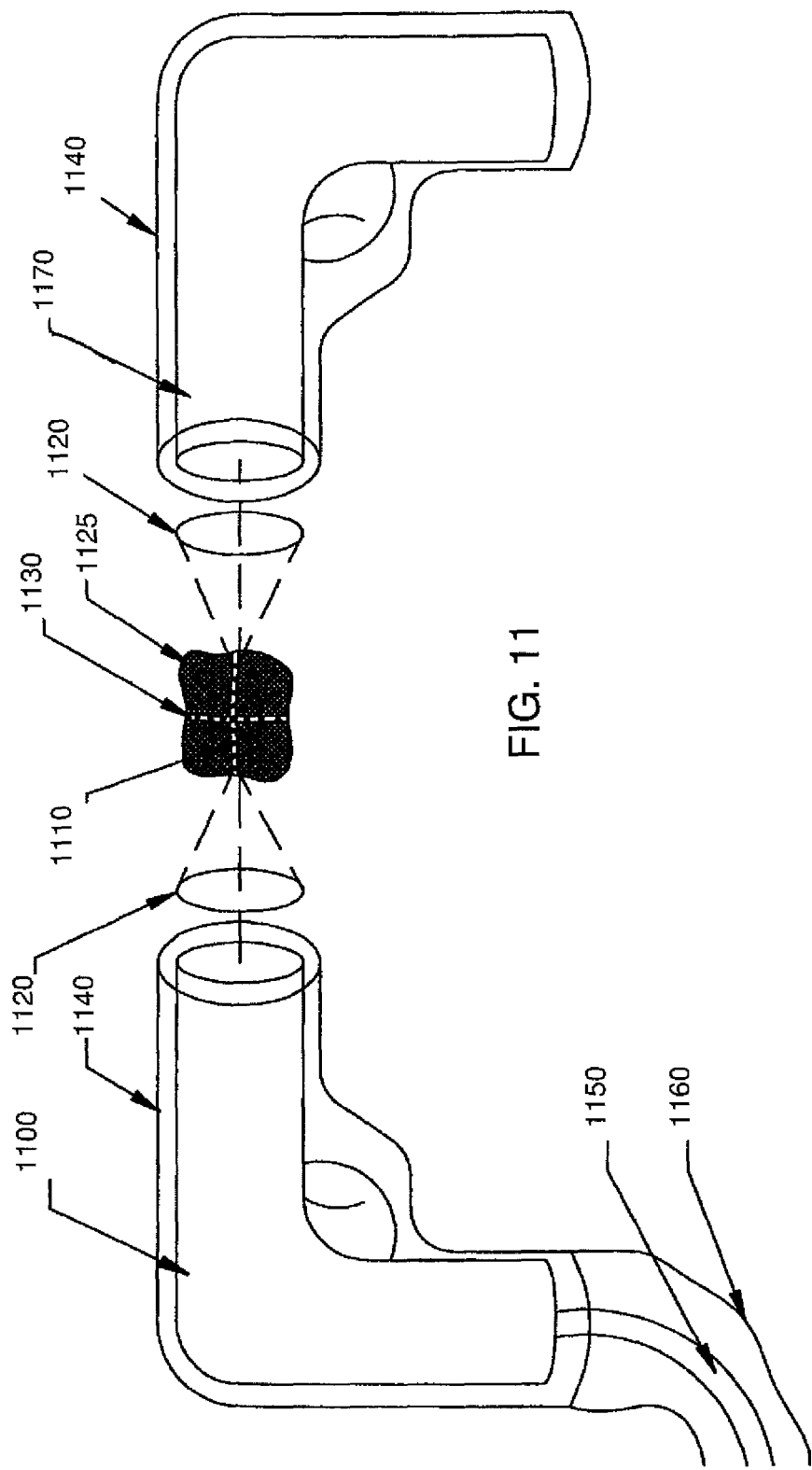
FIG. 11 provides a view of an embodiment of a unique identifier recognition system that can be used to detect a unique identifier on a surgical sponge.

FIG. 11 depicts the use of a handheld detection reader 1100 utilized to detect the unique microscopic identifier barcode label 1110 applied prior to surgery to each sponge 1125. The reader 1100, which can be handheld or mounted, can detect the label 1110 incorporated into thread 1130 woven into the sponge, and transmit the information via cable 1150 to the central processing unit. Also shown is lens 1120. In order to maintain the sterility of the operative field, the detection reader 1100 can be enclosed in a sterile case 1140. In FIG. 11 the connecting cable 1150 is enclosed in a sterile sleeve 1160. FIG. 11 also shows the handheld detection reader 1170 enclosed in a sterile case 1140 to maintain the sterility of the operative field. The reader 1170 detects the unique barcode label 1110 previously applied to the surgical sponge 1125. With respect to reader 1170, no connecting cable is necessary, because the detected information associated with the unique identifier 1110 of that particular sponge 1125 is transmitted to the central processing unit via any suitable wireless communication format.

Disposal Containers Configures for Label Identification

Systems of the invention may include disposal containers for a variety of surgical items, such as sponges and sharps, where the containers are configured to detect labels applied to the items. Such containers may further include automated shape recognition capability, e.g., as described above. The container may have any suitable shape, such as cylindrical, square, rectangular, etc., and as shown below.

Figure 12A:
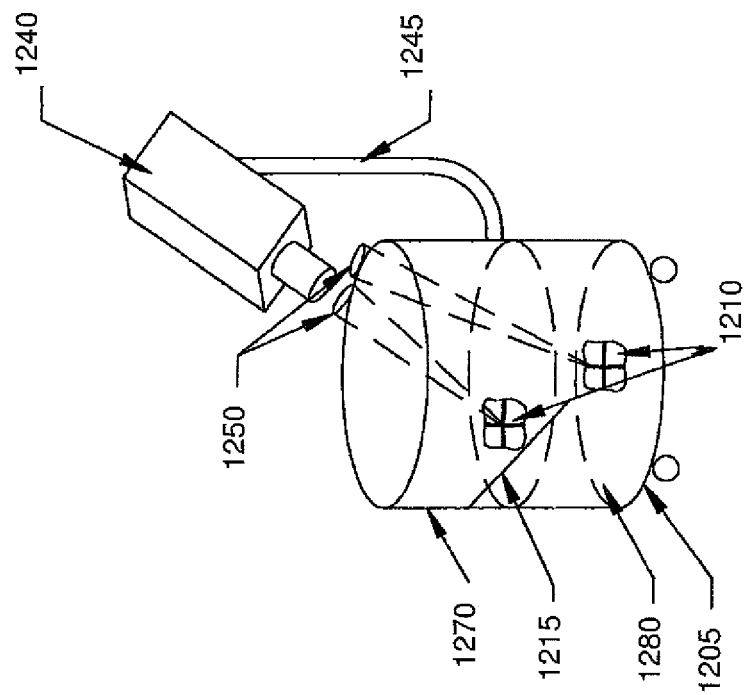
FIGS. 12A-D are schematics of additional embodiments of containers for identification and disposal of surgical sharp objects and sponges, according to embodiments of the invention.
Figure 12B:
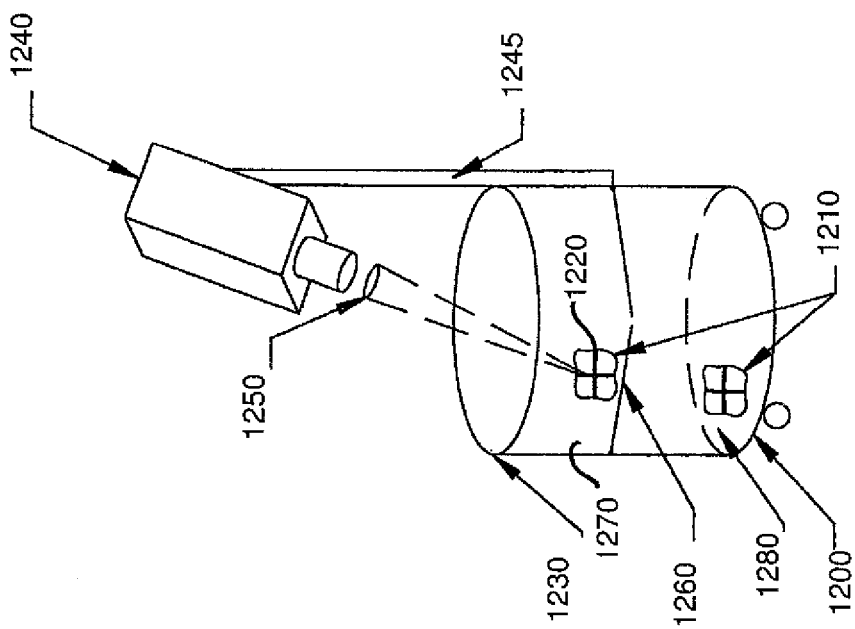

FIGS. 12A to 12B are schematic views of various embodiments of container devices for identifying and disposal of a surgical items, such as sponges and sharps. FIG. 12A depicts an embodiment of a sponge disposal unit 1200 which could be on or off the sterile field, designed to mechanically separate the uncounted discarded sponges from the previously counted and discarded sponges. As a discarded sponge 1210 with an incorporated identifier label 1220 enters the upper portion of the disposal unit 1230, the camera 1240 mounted on control arm mount 1245 detects and identifies the single sponge 1210 via magnifying lens 1250 by unique identifier 1220. In this embodiment, mechanical separation of the uncounted from counted sponges 1210 is achieved by using a trap-door mechanism 1260, which separates the upper disposal unit 1270 (which holds the uncounted sponges) from the lower disposal unit 1280 (which holds the previously counted sponges). Any suitable mechanical separation techniques or electrical, electromagnetic and software or hardware based techniques which can automate the intra-operative counting of surgical sponges, instruments, and/or needles can be used, such as described above. After the sponge 1210 has been uniquely identified and the information captured, e.g., for use by another part of the system such as sponge detection module, the trap door 1260 or other mechanism can facilitate movement of the sponge 1210 into the counted group. Where desired, a power source, either electrical, battery, compressed air or suction, etc., may be employed, e.g., if gravity alone is not sufficient to separate the items.

FIG. 12B depicts another sponge disposal unit 1205 configured to count each sponge 1210 as it is discarded. In this embodiment, the camera 1240 via the magnifying lens 1250 can detect one or more sponges 1210 as they slide down an incline 1215 or alternatively as the sponges 1210 simply enter the lower disposal unit 1280 without any incline. In some embodiments, gravity alone can cause the surgical item to "free-fall" through a detection zone or slide down an inclined plane with or without backlighting. The counting of the sponges in this embodiment can be done without specific mechanical separation of counted and uncounted sponges, because the system is configured to identify the sponge as it enters the disposal unit, and/or the system is configured to account for the time-stamped, counted status of the previously discarded sponges. Therefore, manual recounts of the previously counted discarded sponges are not necessary, which eliminates recounts and re-exposure to blood contaminated items and enhances surgical staff safety.

Figure 12C:
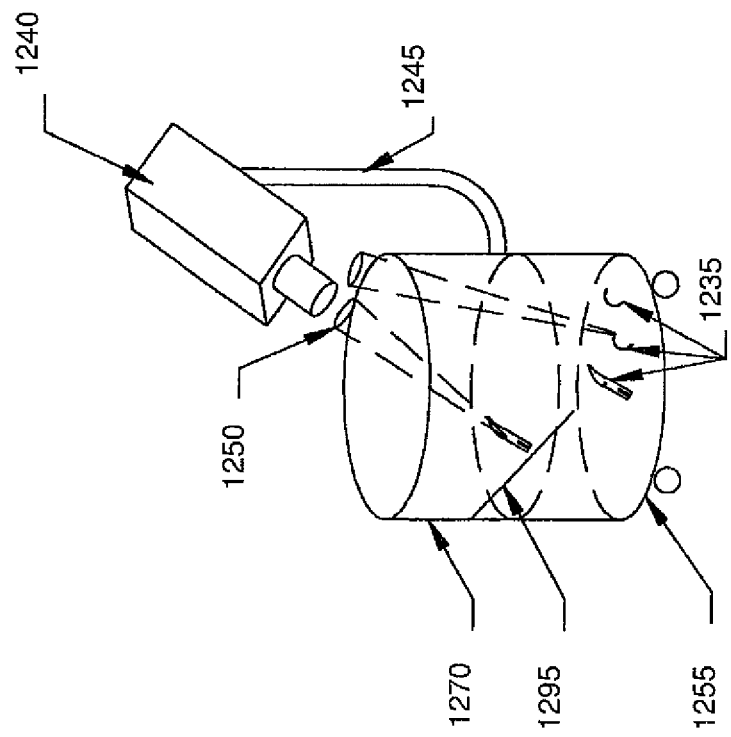

FIG. 12C depicts a surgical sharp object disposal unit 1225 similar to the sponge disposal unit 1200 shown in FIG. 12A which similarly counts each uniquely identified needle or sharp object as it is discarded by mechanical separation of the uncounted sharp objects from the previously counted and discarded sharp objects. As the discarded sharp objects 1235 (e.g., needle or scalpel blade) enters the upper portion of the disposal unit 1270, the camera 1240 via magnifying lens 1250 detects the one or more sharp items with the incorporated identifier. In the lower unit 1280 the previously counted sharp objects are collected for later disposal.

Figure 12D:
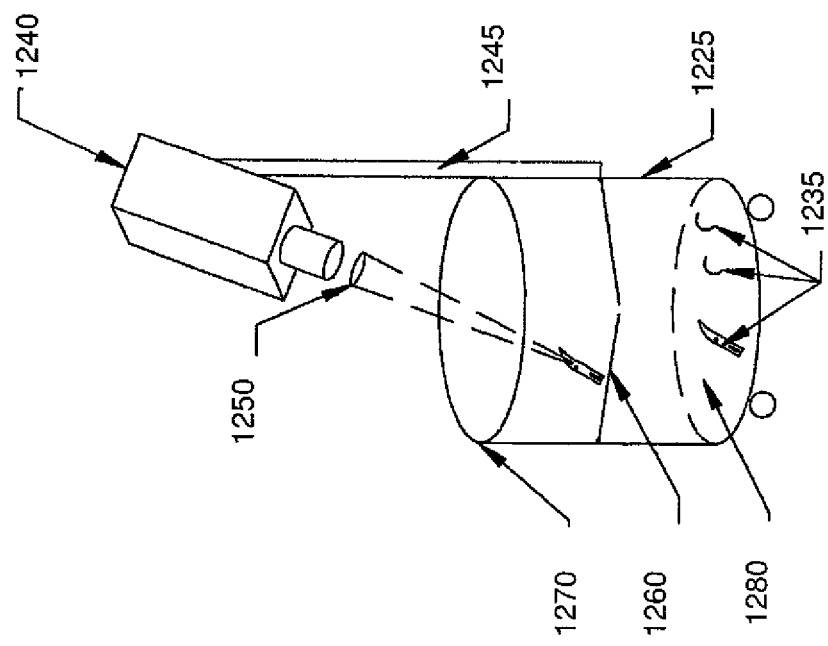

FIG. 12D depicts a surgical sharp object disposal unit 1255 similar to the sponge disposal unit 28 shown in FIG. 4B. In this embodiment, the sharp objects 1235 are detected during gravity-induced "free fall" by identification of the labels associated with the objects. Alternatively the item is detected on the inclined surface 1295 before physically sliding from the upper disposal chamber 1270 into the lower disposal chamber 1280. FIG. 12D also depicts the detection of the discarded sharp objects 1235 on the surface of the lower disposal unit 1280, with or without backlighting of the lower disposal unit 1280, as desired. This embodiment in FIG. 12D, like that of the detection and counting of the discarded sponges 1210 shown in FIG. 12B, can be done without mechanical or physical separation of the discarded sharp items 1235 because the system is configured to identify a given sharp object as it enters the disposal unit, and/or the system is configured to account for the time-stamped, counted status of the previously discarded sharp items present in container 1255. Therefore, manual recounts of the previously counted discarded sharp objects 1235 are not necessary, which improves surgical staff safety.

Figure 15:
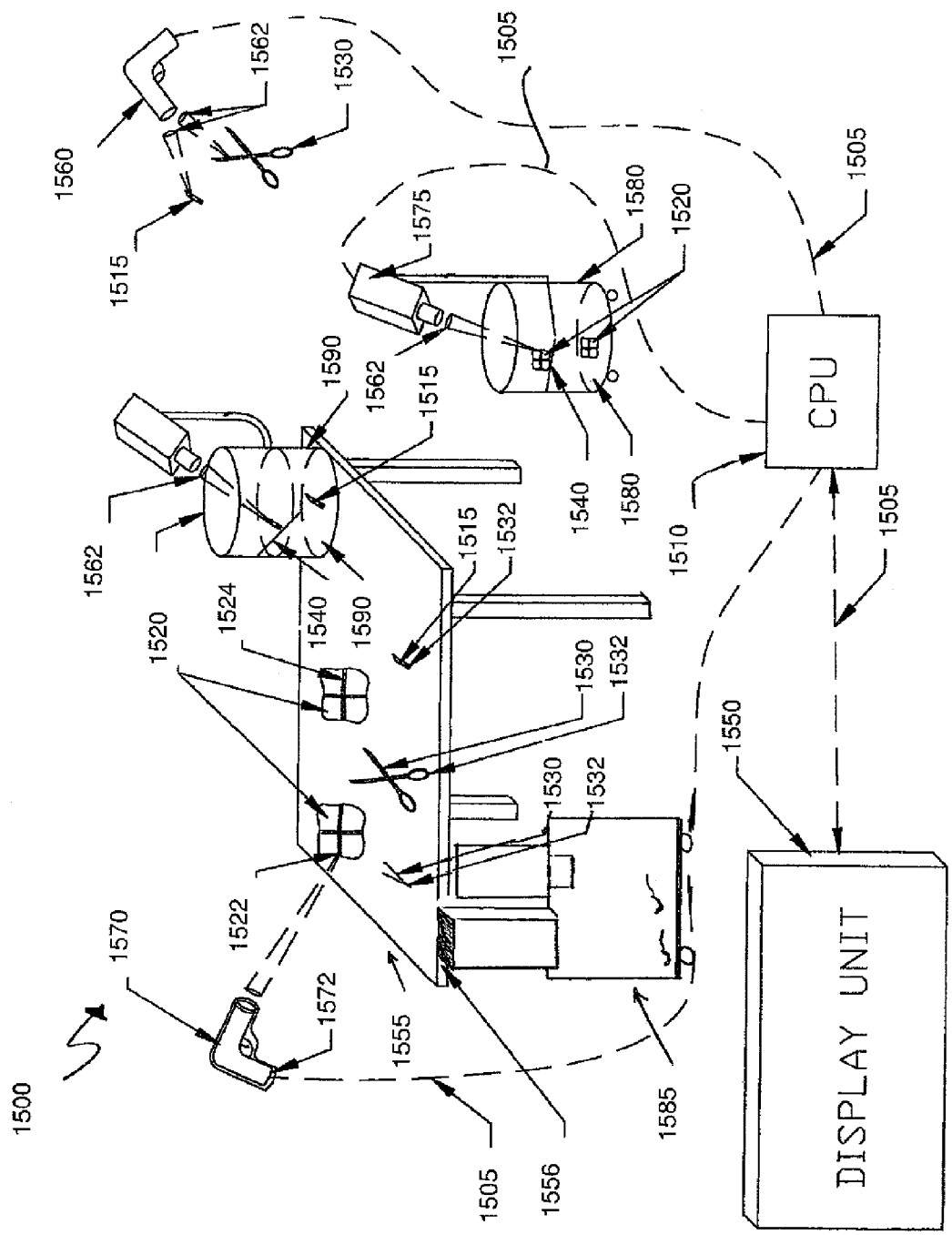
FIG. 15 provides another view of the automated detection and tracking system designed to continuously track surgical sponges, instruments and/or sharp objects, showing integration with a processor and display unit, according to an embodiment of the invention.

In some embodiments, the disposal container can be entirely located within a sterile field (e.g., on top of a sterile back table), or it can be entirely located in a non-sterile field (e.g., on the floor of the operating room). In some embodiments, portions of the container can be both in a sterile field and in a non-sterile field (e.g., a container may have an opening with a chute which is configured to be on or in the sterile field, which leads to the remainder of the container which is positioned in a non-sterile portion of a room). In this embodiment, the disposal container can have a chute, such as shown in FIG. 15, on the side of the table such that the top of the chute is flush with the top of a table. In some aspects, the chute can be straight, as shown in FIG. 15, and in some embodiments the chute can be angled. The chute can be any suitable length to allow the opening of the chute to be on or in the sterile field, with the remainder of the container in a non-sterile field. In some embodiments, the chute can be fixed to a portion of the table (e.g., the ledge, or a table leg, etc.) to secure the chute and disposal container to the table. Any portion of the disposal container and chute can be used with a sterile sheath as necessary.

In some embodiments, the disposal containers can be used with an integrated table. By integrated table is meant a table that can be used during a surgical procedure, such as a sterile surgical back table, that is configured to receive the disposal container. An integrated table can have, for example, a square-shaped box on top of the table configured to receive a disposal container, or the box can be under the table, accessed through a slot in the table, or it can be located on the side of the table such that the top of the container is flush with the top of the integrated table, etc. The area of the table configured to receive the disposal container can be any suitable shape such that the disposal container fits inside, such as square, rectangular, round, etc. In some embodiments, the portion of the integrated table that is on or facing the sterile field can be sterile, such that the disposal container itself does not have to be sterile. In some embodiments, the integrated table can include a chute, such as shown in FIG. 15, on the side of the table such that the top of the container is flush with the top of the integrated table, or a chute that is accessed from a slot in the middle of the table. In this embodiment, the disposal container can be positioned such that the opening to the disposal container is at the end of the chute. By integrated is meant that the elements of the table configured to receive or accommodate the disposal container, such as a box on top of the table, a box under the table, a slot or chute in the table, etc., cannot be separated from the table without irreparably altering the table.

System Configurations

Figure 13:
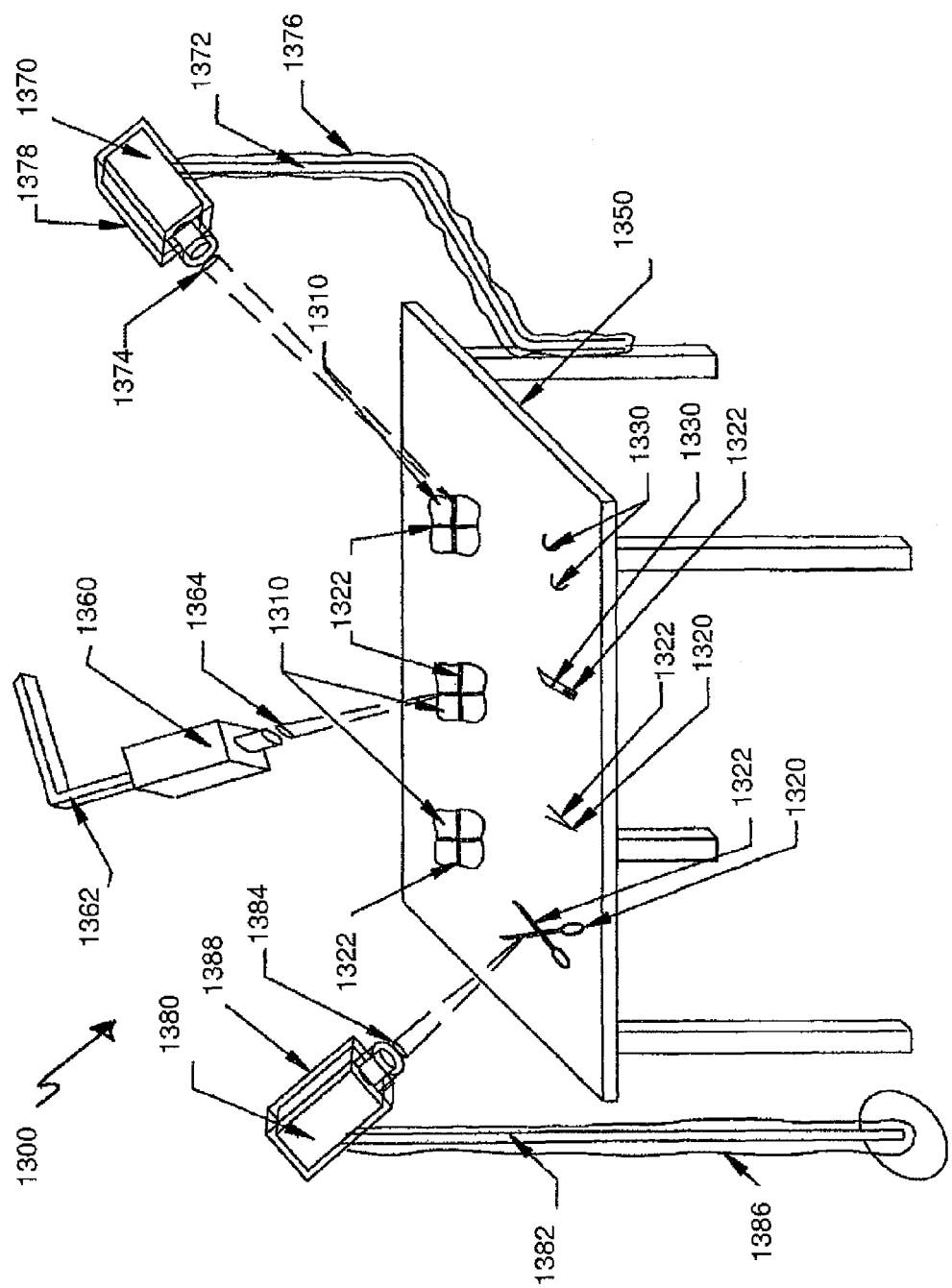
FIG. 13 is a schematic of an automated detection and tracking system designed to continuously track surgical sponges, instruments and/or sharp objects according to an embodiment of the invention.

An embodiment of a system in accordance with the invention is shown in FIG. 13. FIG. 13 depicts a schematic of an automated system 1300 configured to continuously intraoperatively monitor the presence or absence of surgical items, such as instruments, sponges and surgical sharp objects, during a surgical procedure. The surgical sponges 1310, instruments 1320, and sharp objects 1330 labeled with macroscopic or microscopic labels, as desired, can be placed on the sterile surgical back table 1350 used by the scrub nurse to place sponges, instruments or sharp objects prior to their use by the surgeon as the surgeon calls for them. As depicted in FIG. 13, one or more still or video cameras are placed relative to the table 1350 to function as detectors to keep the field of the table under constant surveillance, automatically detecting and recording the unique labels previously placed on the sponges 1310, instruments 1320, and sharp objects 1330 prior to the operation. Also shown are unique identifiers 1322.

In addition to the cameras over the sterile back table, cameras can also be placed in position to monitor the operating field, as well as the "mayo stand", the special instrument tray where the scrub nurse keeps instruments that the surgeon is immediately using. The cameras/readers may or may not move or pan, depending on the camera design, to constantly count and recount and record the surgical items on the table. In some embodiments, the "mayo stand" or sterile surgical back table can have markers which delineate a grid on the table, such that markers can outline areas where a particular camera/reader may scan. The camera(s) may be mounted in a variety of ways. Three possible mountings of the cameras/readers are shown in FIG. 13, though many others are possible. For example, one camera 1360 can be mounted on a control arm mount 1362 attached to the ceiling or wall above or to the side of the sterile field. Another camera 1370 can be mounted on a control arm mount 1372 attached to the legs of the table 1350. Another of the multiple options for camera mounting is depicted by another camera 1380 placed on a movable control arm 1382, which has a freestanding base, which may or may not be on wheels. Any suitable system for mounting the reader/cameras for the automation of counts of surgical items can be used. However, if mounted or held close to the sterile operating field, a sterile case (1378, 1388) and sheath (1376, 1386) may be employed to maintain the sterility of the operative field and table 1350, as desired. If magnification is necessary, a lens (1364, 1374, 1384) can be utilized, which in some embodiments can be incorporated into the case 1378 or 1388. Alternatively, a digital microscope can be used to magnify and detect the unique labels applied or etched into the surgical items.

Figure 14:
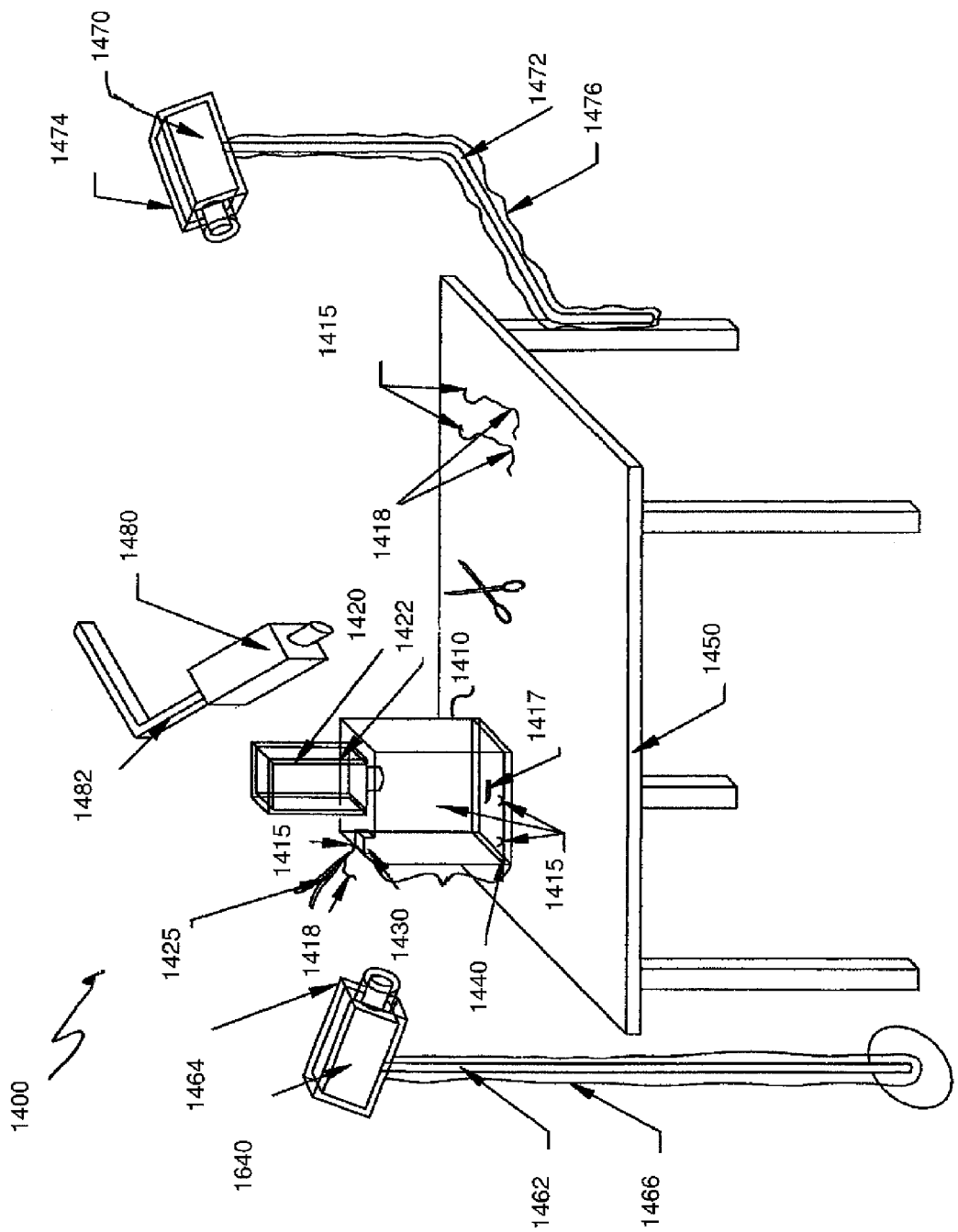
FIG. 14 provides another view of an automated detection and tracking system designed to continuously track surgical sponges, instruments and/or sharp objects which also includes a container for identification and disposal of a surgical sharp object, according to an embodiment of the invention.

FIG. 14 is a schematic of an automated system 1400 configured to continuously monitor the presence or absence of surgical sharp objects by constant video monitoring of the sterile operative field, as well as other surgical items by various means. Items can be counted into the system and tracked via repeated detection events or continuous video monitoring and counted as off the field by disposal into device for identifying and disposal of a surgical sharp object or counted by a hand-held or portable device if the needle or other sharp object falls from the sterile field. As shown, system 1400 includes sharps automated shape recognition disposal container 1410, which is analogous the containers described above, e.g., see FIGS. 2A-2D. Container 1410 includes an imaging device 1420 for obtaining image data of an item that has been placed into the container, and a processor configured to identify the surgical sharp object using the image data by automated shape recognition. Also shown are needle holder 1425 holding needle 1425 with attached suture 1418, prior to being dropped into chute 1430 of the sharps automated shape recognition disposal container 1410, where they fall onto horizontal platform 1440. In FIG. 14, surgical needles 1415 and other sharp objects such as scalpel blades 1417 are placed on the sterile back table 1450 used by the scrub nurse to place instruments and other items such as needles 1415, sutures 1418 and sponges prior to their use when the surgeon calls for them. As discussed above, the subject system allows the surgical personnel to place the surgical items as used currently. No particular placement or arrangement is needed for the system to track the surgical items. One or more still or video cameras can function as readers or scanning camera devices (e.g., sterile camera/readers 1460 and 1470, non-sterile camera/reader 1480, or sterile camera/reader in container 1420) to keep the table 1450 under constant surveillance, automatically detecting and recording the unique 1D barcodes or 2D barcodes, or needle shape or 3D visualization of the sharp items (e.g., needles, scalpel blades). The cameras or barcode readers may or may not move or pan, depending on the camera design, to constantly and continuously count the needles and other sharp items such as scalpel blades. The embodiment shown in FIG. 14 depicts three mountings of the devices, similar to those shown in FIG. 13. For example, one camera 1480 is mounted on a control arm mount 1482 attached to the ceiling above or to the side of the sterile field. Another camera 1470 is mounted on a control arm mount 1472 attached to the legs of the table 1450. Similarly, another camera/reader 1460 is placed on a movable control arm 1462, which has a free-standing base. The movable camera/reader can allow the camera to be positioned as desired; e.g., over the operating table. Again, a sterile case 1422, 1464 and 1474 and connecting sheath 1476, 1466 may be present, as desired, to maintain the sterility of the operative field and table 1450.

FIG. 15 depicts the overall integration of a system 1500 and in particular, the flow of information 1505 to and from a central processing unit 1510 of the system. The operating room personnel are kept informed of the pre-operative and current counts of surgical sponges 1520, surgical instruments 1530, and surgical needles or other sharp objects 1515 in real-time via one or more display units 1550, which may be in the form of LED, LCD, plasma or cathode ray monitors, among other types, as desired. The non-sterile handheld camera or scanning devices 1560 held by the circulating nurse or the handheld scanner 1570 with lens 1562 enclosed within a sterile case 1572 and operated by the scrub nurse can detect the presence or absence of a unique identifying labels 1522, multiply incorporated into thread 1524, which has been woven into a sponge 1520. Also shown are identifying labels 1532 on instruments 1530 and surgical sharp objects 1515. Needles or other sharp objects, and instruments are identified in a similar manner. The identifying information 1505 is transmitted via cable or wirelessly to the central processing unit 1510. The information 1505 is time-stamped indicating whether or not the sponge 1520, or sharp objects 1515 were present at any particular time during the operation. The information is then transmitted to a display unit 1550, such as a flat panel LED or plasma monitor. The information is then displayed for all pertinent personnel present at the operation to see. Any discrepancy in the count is then clearly indicated on the display unit 1550.

Sponges 1520 dropped or discarded from the operative field are scanned and identified as off the field, or "checked out" by the circulating nurse using a non-sterile reader 1575 or simply discarded into a sponge disposal unit 1580, which is analogous to the sponge disposal units as described above. Needles or other sharp objects dropped or discarded from the field, but not in the disposal container chamber 1590, are scanned off the field by the circulating nurse using a non-sterile camera or scanner 1560. If the sharp object is no longer needed it is simply discarded into a sharp disposal unit 1590, which can be kept sterile for ease of use by the scrubbed personnel or it could be non-sterile and off the field. Needles or other sharp objects appropriately discarded into the disposal unit are also counted as off the field, or "checked out". In some embodiments, surgical sharp objects, instruments, or sponges can be "checked out" by being placed into a chute 1556. In this embodiment, the upper portion of the chute 1556 containing the opening is sterile, and is located in the sterile field (e.g., the sterile back table). The lower portion of the chute is in the non-sterile portion of the room (e.g., operating room). The surgical sharp objects, instruments, or sponges can then fall into disposal container 1585 from the sterile opening in chute 1556 to the portion of the container with non-sterile reader 1575 which is in the non-sterile portion of the room. Instruments 1530 dropped or discarded from the operative field are scanned and identified off the field by the circulating staff using a non-sterile reader 1560. Unless re-sterilized and returned to the field and rescanned into the field by the scrub nurse and the sterile reader 1570, the discarded instrument 1530 is considered by the recording system and central processing unit 1510 and operating room staff to be no longer on the operative field. Although not shown in FIG. 15, in some embodiments a visual signal (e.g., photochromic dye) can be used in addition to the counting information on display monitor 1550 identified via optical recognition of the specific surgical item.

In some embodiments, the system can be configured to recognize a non-unique identifier on a surgical item. By non-unique identifier is meant an identifier which identifies a particular type of surgical item, e.g., a forceps, or a retractor. In some embodiments, the "inbound" or "outbound" count of a surgical sharp object, instrument, or sponge can be performed by detecting a non-unique identifier. For example, a scrub nurse can scan a non-unique identifier on ten clamps, such that ten clamps are "checked in" to a surgical procedure.

In some embodiments, the "inbound" count, the "outbound" count, or tracking of a surgical sharp object, instrument, or sponge can be performed using an "automated assistance" feature. By automated assistance is meant that a surgical item is visually identified by operating room personnel, followed by selecting and then scanning an appropriate code, such as a bar code, which corresponds to the surgical item from a menu of codes. Embodiments can also include an option to select and then scan a bar code which corresponds to the number of items that have been visually identified and counted. For example, a package of ten 4-0 Prolene™ needles may be visually identified, and the bar code encoding "4-0 Prolene™ needles" may be scanned, followed by scanning of the bar code for the number "ten". Similarly, five curved forceps may be visually identified and counted, and the bar code encoding "curved forceps" may be scanned, followed by scanning of the bar code for the number "five". In some embodiments, the bar code for a particular item can have an associated image, e.g., a photo of a curved forceps, next to the bar code to help operating room personnel in location and identifying a particular surgical item. In this way, the automated assistance feature can increase the accuracy of traditional counting methods.

In all cases, the surgical item present and counted into the operation must be accounted for at the final count or it is considered a possible retained foreign surgical body (RFSB). In cases where an item is determined to be missing, areas such as the table 1555 or the disposal units 1580 or 1590 can be rescanned to verify if a surgical item (e.g., needle) is truly missing. If the surgical item is not found, an additional search of the patient (e.g., including xray) or areas around the patient, such as in the surgical drapes or the floor, can be made to locate the surgical item.

Central Processing Unit

The Central Processing Unit (CPU) can integrate all the data of the automated system. The various components of the system include integration of the information from any and all sources, including devices for identifying and disposal of a surgical sharp object, the one or more readers/cameras, information provided by one or more modules (e.g., an automated shape recognition module; a unique identifier recognition module; a surgical instrument tracking module; a surgical sharp object tracking module, a surgical sponge tracking module etc.) data entered by operating room personnel including hand-entered or voice-entered data, and can maintain accurate counts displayed on the monitor for all essential operating room personnel to see.

In certain embodiments, a system includes hardware components which take the form of one or more platforms, e.g., in the form of servers, such that any functional elements of the system, i.e., those elements of the system that carry out specific tasks (such as managing input and output of information, processing information, etc.) of the system may be carried out by the execution of software applications on and across the one or more computer platforms represented of the system. The one or more platforms present in the subject systems may be any convenient type of computer platform, e.g., such as a server, main-frame computer, a work station, etc. Where more than one platform is present, the platforms may be connected via any convenient type of connection, e.g., cabling or other communication system including wireless systems, either networked or otherwise. Where more than one platform is present, the platforms may be co-located or they may be physically separated. Various operating systems may be employed on any of the computer platforms, where representative operating systems include Windows, MacOS, Sun Solaris, Linux, OS/400, Compaq Tru64 Unix, SGI IRIX, Siemens Reliant Unix, and others. The functional elements of system may also be implemented in accordance with a variety of software facilitators, platforms, or other convenient method.

The CPU can include an "assisted identification" feature, which can be a separate component or part of any of the tracking modules disclosed above, such that data entered by operating room personnel including hand-entered or voice-entered data in some instances can be in response to a choice presented by the CPU; for example, if a twisted or bent needle has been dropped into a disposal container and the surgical sharp object tracking module is able to narrow the options down to four or fewer, or three or fewer options, the operating room personnel can then be presented with a choice e.g., three options of needle types. The operating room personnel (e.g., a scrub nurse) can then select the type of needle that was just discarded so that an accurate count and tracking of the needle is kept. In some instances, the auto-assist feature can be used in instances when a tracking module is unable to definitively identify a surgical item.

In other embodiments, as in the automated assistance feature disclosed above, once a surgical item has been identified or detected, the CPU can include an image of the surgical item for confirmation. The image can be displayed at the detector where the surgical item is detected, or at any display unit in the system. For example, if a unique identifier on a hemostat is scanned by a hand-held scanner at a sterile back table, the hand held scanner can display a likeness of the hemostat, which can be seen by the operator (e.g. scrub nurse) before the count of the hemostat is confirmed and added to the system. Inclusion of a likeness or image of the surgical item to be counted or tracked can also be used in embodiments where the surgical item has an identifier that identifies the type of surgical item (e.g., retracter) but that is not unique, or in instances in which a surgical item is visually identified and then the appropriate bar code is scanned, as discussed above.

In addition to hand-entered (e.g., using a keyboard) or voice-entered data (e.g., using speech recognition software), including notes on the procedure or count, etc., the CPU can also accept patient and staff information by scanning badges or identification bracelets, etc. The CPU can therefore integrate information on all personnel present in the operating room at a particular time, and can track staffing changes.

In addition, the CPU can integrate the other functions of the system and/or integrated with other systems including but not limited to inventory, billing, ordering, electronic medical record-keeping, and comparing with protocol. The system can also be used for medicolegal records. For example, if a count discrepancy is found, the system can provide a record of the count as well as record the surgeon's decision (e.g., to re-explore the wound, obtain an X-ray, etc.) for any future medicolegal question easily retrievable. The system also provides a record of the counts, and a record of the operating room personnel responsible for the counts.

Display

The display units of the subject invention can be any convenient type of monitor operatively coupled to a CPU and can be of any convenient size suitable to allow visualization by key operating room personnel. The display unit can be freestanding; e.g., can be placed on a table, or it can be mounted to a stand or a wall in any convenient location. In some embodiments, there can be more than one display unit that displays all the current real-time tracking information. In addition, in some embodiments there can be additional display units that can display only some of the tracking information, such as for example with a device for identifying and disposing of a surgical sharp object which can have a monitor displaying the real-time count of surgical sharp objects that have been discarded into the container. A display unit can therefore be configured to display real-time tracking information for a surgical item, such that the display can include information on the current count, current location, etc. of any surgical item such as a surgical instrument, surgical sharp object, or surgical sponge. A display unit can also include an attached device for input of data, verification of counts, electronic signatures, etc., such as a keyboard. A display unit can further have a sterile covering to allow placement of the display unit on a sterile field.

Figure 16:
FIG. 16 is a schematic of the large panel display of a real-time instrument count indicating the presence or absence of any particular instrument at any time during a surgical procedure, according to an embodiment of the invention.

FIG. 16 is a schematic of the large panel display 1600 of an instrument count indicating the presence or absence of any particular instrument at any time during an operation, as indicated by the information processed by the central processing unit. The data shown on the display screen can include the name of the instrument (e.g., tissue forceps), and the total number of similar instruments still on the operative field, and the number of similar instruments that have been "checked out". The detection of any particular instrument during the operation or after the operation is continuously compared to the original count and the count of instruments already removed from the field. Any discrepancy is noted on the display prominently mounted for all operating personnel to see. The display screen can also note the operating room personnel present, and the identification of the personnel who verify the surgical item count or counts.

FIG. 17 shows another view of the large panel display 1700 showing a needle and sharp object count indicating the presence or absence of the sharp objects at any time during the operation, as indicated by the information processed by the central processing unit. The data shown can include the number of a particular size and type of needle and suture, or the particular other sharp object being counted. The detection of any particular needle type or suture type is automatically compared to the number of similar surgical items counted originally, and the current real-time count of similar surgical items counted by the camera mounted above the disposal chamber and/or dropped from the operative field and counted off the field with the non-sterile handheld scanner or separate non-sterile detection and disposal chamber. The system thus automatically detects the presence or absence of the needles and other sharp objects.

FIG. 18 depicts an embodiment of the panel display 1800 showing counts of sponges, instruments, and sharp objects which have been registered for the particular operation. The detection of any particular counted surgical item, such as a sponge, instrument or sharp object, during the operation or after the operation is compared to the original count and the count of the items already removed from the field. The presence or absence or any of these items, or class, is kept current by any number of rescans or constant still camera or video surveillance is also possible depending on the technology utilized. Any discrepancy is noted on the display prominently mounted for all operating room personnel to see. Although the display monitor embodiment shown in FIG. 18 for convenience displays data for three types of surgical items (i.e., for "sponges", "instruments" and "sharps"), the display screen can display as many lines of data or entries as are needed for a particular operation. For example, in some embodiments, there may be three types of sponges displayed, seven types of needles displayed, 10 types of instruments displayed, etc. Therefore, the number of surgical item counts displayed and/or lines of data displayed can be four or more, such as 8 or more, or 15 or more, or 20 or more, etc.

Methods

The subject methods include a method of intra-operatively identifying a surgical sharp object. Aspects of the methods include obtaining a surgical sharp object from an operative sterile field, imaging the surgical sharp object with an intra-operative imaging device to obtain image data, imaging the surgical sharp object with an intra-operative imaging device to obtain image data, and forwarding the image data to a surgical sharp object automated shape recognition module configured to identify the surgical sharp object from the intra-operative surgical sharp object image data. Imaging the surgical sharp object can include placing the surgical sharp object in the range of an intra-operative imaging device configured to obtain image data, which can include placing the surgical sharp object into a container configured for disposal of the surgical sharp object, placing the surgical sharp object onto a sterile table, such as an operating room table or a sterile back table, or placing the surgical sharp object within in the range of a hand-held imaging device.

The subject methods can further include tracking of a surgical sharp object. Tracking of a surgical sharp object can include placing the surgical item within the range of a detector, and identifying the surgical item or items by sensing a unique identifier (e.g., by reading the bar code on a package of needles). Tracking can include information on the location of the surgical sharp object, as well as the time that an object was identified by a particular sensor or detector. Tracking can therefore include detecting and identifying a surgical sharp object and following the location of the surgical sharp object for a period of time, for example, during "check-in" or "inbound" count, or for the duration of a surgical procedure, or for "check-out" or "outbound" count, etc. Tracking of a surgical sharp object can also include identifying a surgical sharp object by automated shape recognition using image data, as discussed above. In some embodiments, identification of the surgical sharp object by automated shape recognition is performed dynamically.

In addition to tracking of a surgical sharp object, the methods can also include tracking of a surgical item, such as one or more surgical instruments and/or one or more surgical sponges. Tracking of a surgical item such as a surgical instrument or sponge can include placing the surgical item within the range of a detector, and identifying the surgical item or items by sensing a unique identifier (e.g., by sensing electro magnetic identification (EMID) label on a sponge). Tracking can include information on the location of the surgical item, as well as the time that an item was identified by a particular sensor or detector. Tracking can therefore include detecting and identifying a surgical item and following the location of the surgical item for a period of time, for example, during the initial registration or "check-in" or "inbound" count of a surgical item, during the final count or "check-out" or "outbound" count, or for a period of time during a surgical procedure, such as 30 minutes, or 60 minutes, or the entire duration of the procedure, etc.

In some embodiments, tracking of a surgical sharp object, a surgical instrument or a sponge is accomplished via multiple detection events (e.g., the surgical item is detected at the beginning and end of a surgical procedure), or by continuous video monitoring (e.g., the surgical item is placed on a sterile back table, and is continuously monitored during a surgical procedure). In some embodiments, tracking of a surgical sharp object, a surgical instrument or a sponge can include both single detection events as well as continuous video monitoring.

In the subject invention, identifying and/or tracking can be done with a detector, such as a hand-held or mounted detection device. One or more detectors can be used by the operating room personnel to count each surgical item at the beginning of a surgical procedure. For example, a hand-held detection device enclosed in a sterile disposable case can be used to detect a labeled item; e.g., a 1D or 2D unique barcode previously laser etched onto an instrument itself. The initial count may be performed of the actual object (e.g., Metz scissors) or its packaging (e.g., a package containing ten 3-0 needles). Once completed, the count can be electronically accepted by operating room personnel such as the scrub nurse and circulating nurse. Electronic acceptance of a count can be an electronic record of the accepted count, or a paper record of the count can be generated, or both an electronic and a paper record. The electronic or paper records can comply with any legally mandated privacy laws and regulation (e.g., HIPAA regulations). A comprehensive time-stamped inventory of all instruments utilized for the case can therefore be generated.

Tracking can include tracking of one or more surgical sharp objects, surgical instruments, or surgical sponges. Tracking of surgical items can be performed by a module (i.e., a combination of hardware and/or software which will perform a tracking function) such as a surgical instrument tracking module, a surgical sponge tracking module, or a surgical sharp object tracking module, etc.

Once an initial count of all surgical items to be used in the surgical procedure has been made, the count is kept accurately during the procedure, as sponges, instruments and sharp objects are added or removed from the field during the case. Each addition or removal of an item from the sterile operating field thus is counted by the detection system and is tracked and counted appropriately. The count information can be displayed in a real-time manner on a display unit for all operating room personnel to see. The subject methods can also record the acceptance of responsibility for the counted sponges, instruments and sharp objects both by the scrubbed personnel and the circulating operating room personnel. Finally, an electronic digital record of the count generated by the invention can be entered into an electronic database for the operation and kept for future medical and medico-legal reference.

The description of the present invention is provided herein in certain instances with reference to a subject or patient. As used herein, the terms "subject" and "patient" refer to a living entity such as an animal. In certain embodiments, the animals are "mammals" or "mammalian," where these terms are used broadly to describe organisms which are within the class mammalia, including the orders carnivore (e.g., dogs and cats), rodentia (e.g., mice, guinea pigs, and rats), lagomorpha (e.g., rabbits) and primates (e.g., humans, chimpanzees, and monkeys). In certain embodiments, the subjects, e.g., patients, are humans.

Utility

The methods and devices of the subject invention can be used with any surgical or other invasive procedure, including but not limited to procedures conducted in the operating room, or outpatient surgery center, or any procedure where correct counts of surgical items is desired. As discussed above, the counts of surgical items can be continuously monitored, however a record of the counts at any point in time during the procedure or operation, for example, with verifying electronic signatures, can be performed before surgery begins, after surgery has concluded, or at any time during the procedure. Counts can also be performed before any type of hollow organ closure (e.g., closure of an intestinal loop, cardiac chamber, peritoneum, etc.) or before wound or skin closure, etc.

Currently, most hospitals have policies in effect requiring that surgical personnel visually and audibly count the sponges and other textile-based objects, the surgical instruments, and the surgical needles and other sharp objects and then hand record the results of the counts to prevent the retention of a sponge, instrument or sharp object. Depending on the complexity and length of time of the operation, current counting methods take two nurses approximately 15-30 minutes of audible manual counting per count per operation. The opportunities for errors in the count are numerous and obvious in a system designed to rely on human manual counting and pencil and paper recording methods alone. In addition, the needles and sharp objects have to be kept on the field for ongoing and final counting, even though they are not to be used again, which increases the risk of exposure to injury and blood-borne illness.

The automated nature of the current system utilizes highly accurate methods of detection, recordkeeping and records of operating room personnel, in a time-stamped non-alterable manner. Responsibility for the counts is clear, and avoids the need for later reconstruction of who might or might not have been present in the operating room during any particular part of the operation. Any decisions made by the surgeon in cases of a count discrepancy is similarly recorded, making any future medicolegal question about the reporting or non-reporting of results and decisions regarding incorrect counts easily retrievable. The accuracy and designation of responsibility for the counts and decisions affected by the count are all improved by the subject methods and system.

Most importantly, the chances for errors are reduced and the likelihood of incorrect counts reduced. Safety is greatly enhanced for the patient, who is less likely to be exposed to unnecessary radiation to detect a retained foreign body. The patient is also less likely to be subjected to an unnecessary re-exploration of the body cavity. In addition, safety is enhanced for all patients, because the time spent in the operating room counting and recounting surgical items is reduced, thereby reducing operating time for all procedures. The current system also decreases the likelihood of complications from a retained surgical foreign body, because the incidence of retained surgical foreign bodies is reduced. In addition, increased accuracy of the count improves the safety of the operating room staff who will face less radiation exposure and less exposure to blood contaminated items, especially the sponges and sharp objects which are presently counted and recounted manually several times during an operation. Finally, the clear time-stamped unalterable nature of the count information and the display of the information in current time during the operation make the recordkeeping of the count and the clear acceptance of responsibility automatic. The enhanced medical record and medico-legal record of the surgical items counted are a further benefit as the responsibility of the decision makers is automated and accepted in real time as the decisions are made. The overall result is a safer operation for the patient and for the operating room personnel and less medico-legal exposure for the institution.

The official record of the count can also be used for inventory, billing, ordering, electronic medical record-keeping, or medico-legal purposes. For example, the inventory control of various sizes and/or types of instruments, etc., may be improved by integrating the scanned data can be transmitted directly to the hospital inventory control system or to the appropriate product vendor for automatic reordering.

For medical record-keeping or medico-legal purposes, a record of the assignment of responsibility for surgical item counts can include verbal recorded agreement assigned by machine and accepted at the conclusion of the procedure by barcode reading or by voice recognition of digitally recorded voices of the personnel involved. Ultimately, all of the pertinent information of the count, the responsible parties performing the count and results of decisions based upon the count results are easily placed in the digital electronic medical record produced by the central processing unit at the completion of the operation. Counting errors, recording errors, and even handwriting errors are thus eliminated providing documentation easily retrieved for medical or medico-legal reasons.

The current system also fits well with currently accepted protocols, which leads to ease of use and acceptance of the system by operating room personnel. For example, current counting protocol requires the agreement by two members of the operating room staff on the initial and final counts and any changes during the operation, similar to the methods of the subject invention. Additionally, using the current system, no particular placement or arrangement of instruments on the surgical table is needed, in contrast to methods which use mechanical tray counting systems or other sensing modalities dependent upon a particular spatial arrangement. The current system permits the surgical personnel to place the items as desired, according to current protocol in all operating rooms. The ability to place instruments, etc., in their accustomed positions is advantageous because the arrangement of surgical implements in most operating rooms is determined by the personal preference of the scrub nurse. Using the current methods, the scrub nurse or technician is not required to re-train or follow a particular protocol, which could affect the surgeon's call for particular items. The current methods enhance the safety and speed of the operation as the scrub personnel are not preoccupied with manual counting while still carrying on the physical actions of the operation, which present day counting processes require.

Computer Readable Storage Medium

Aspects of the invention further include physical storage medium containing programming or instructions for carrying one or more of the tasks of a system of the invention, e.g., as described above. "Computer readable storage medium" as used herein refers to any storage or transmission medium that participates in providing instructions and/or data to a computer for execution and/or processing. Examples of storage media include floppy disks, magnetic tape, USB, CD-ROM, a hard disk drive, a ROM or integrated circuit, a magneto-optical disk, or a computer readable card such as a PCMCIA card and the like, whether or not such devices are internal or external to the computer. A file containing information may be "stored" on computer readable medium, where "storing" means recording information such that it is accessible and retrievable at a later date by a computer. A file may be stored in permanent memory.

With respect to computer readable media, "permanent memory" refers to memory that is permanently stored on a data storage medium. Permanent memory is not erased by termination of the electrical supply to a computer or processor. Computer hard-drive ROM (i.e. ROM not used as virtual memory), CD-ROM, floppy disk and DVD are all examples of permanent memory. Random Access Memory (RAM) is an example of non-permanent memory. A file in permanent memory may be editable and re-writable.

To "record" data, programming or other information on a computer readable medium refers to a process for storing information, using any convenient method. Any convenient data storage structure may be chosen, based on the means used to access the stored information. A variety of data processor programs and formats can be used for storage, e.g. word processing text file, database format, etc.

A "memory" or "memory unit" refers to any device which can store information for subsequent retrieval by a processor, and may include magnetic or optical devices (such as a hard disk, floppy disk, CD, or DVD), or solid state memory devices (such as volatile or non-volatile RAM). A memory or memory unit may have more than one physical memory device of the same or different types (for example, a memory may have multiple memory devices such as multiple hard drives or multiple solid state memory devices or some combination of hard drives and solid state memory devices).

The following examples are offered by way of illustration and not by way of limitation.

EXPERIMENTAL

I. Current Operating Room Technique

A patient is prepped for an abdominal surgical procedure and brought into the operating room. The operating room team consists of three operating room nurses, two surgeons, and an anesthesiologist, who are also present in the operating room. The operating room nurses are responsible for tracking the all of the surgical items to be used during the surgical procedure, including instruments (e.g., clamps, forceps, etc.), sharp objects (e.g., scalpels, needles, etc.), and sponges used during the surgery or surgical procedure. Surgical instruments, needles, scalpel blades, sponges, pads and other objects are lined up on a sterile receptacle or tray and the number and type of each surgical item is counted. The total count of instruments is over 200 individual items, the total count of needles and sharp items is also over 200 individual items, and the total count of sponges is over 600 individual items to be counted.

An initial count of the instruments, needles and other sharp objects, and sponges is done by the scrub nurse by visual and audible counting, which is witnessed visually by the circulating nurse. The initial count takes approximately 25 minutes. The count data for each of the surgical items is entered by pencil into a chart on a clipboard. Once all of the items have been counted and recorded, the surgery begins.

Twice during the surgery when there is a change in personnel, the count of all the surgical implements is repeated by two of the nurses. Each additional count takes 20 minutes each. During the operation, all instruments, unless they become contaminated, are kept either in the operating field on the sterile back table. Used sponges, once saturated with blood or other body fluids, are placed into a bucket to be manually separated and counted by the non-scrubbed, non-sterile or circulating operating room personnel. The discarded sponges are then packaged for later recounts in a clear plastic 'shoe rack' device. Previously used needles and sharps are kept on a magnetic or spongy platform, so that they are available for repeat counts as personnel change or as discrepancies in counts arise. The recounts provide opportunity for injury to staff. Before the stomach is closed, a fourth count which takes 20 minutes is performed, and verified by two operating room personnel.

At the end of the surgery, prior to wound closure, the count is performed for a fifth time. During this count, there is a discrepancy in the number of sponges and it appears that one is missing. The surgeon is informed, and a search is begun for the missing sponge. When the missing sponge cannot be located, the count is repeated. The final count of each of the surgical items matches the initial count and the surgeon decides to accept the final count as the accurate count. The surgery is then completed.

In cases where the discrepancy persists after recounting, the surgeon must decide to whether or not to explore the wound to locate the missing sponge. The surgeon may order an x-ray examination of the patient on the operating room table to rule out the presence of the radio-opaque labeled sponge. If the patient is unstable, the surgeon may feel it is in the best interest of the patient to complete the operation and transfer the patient out of the operating room.

II. Automated Correct Count

Use of Tracking System in a Surgical Procedure

A patient is prepped for an abdominal surgical procedure and brought into the operating room. The operating room team consists of three operating room nurses, two surgeons, and an anesthesiologist. The operating room nurses are responsible for tracking all of the surgical items to be used during the surgical procedure, including instruments (e.g., clamps, forceps, etc.), sharp objects (e.g., scalpels, needles, etc.), and sponges used during the surgery or surgical procedure.

A tracking system as disclosed in FIGS. 14 and 15 is used to track the surgical items used for the abdominal surgical procedure. As the nurses prepare for the surgery, they register each of the surgical items to be used with a hand-held scanner. Specifically, a sterile hand-held scanner 1570 is used for the "inbound" count of all surgical instruments, needles, scalpel blades, sponges, pads and other surgical items, which are lined up on a sterile tray. The number and type of each surgical item is scanned into the system.

As each of the items is registered, the nurses double check the information as it appears on the display unit 1550 of the tracking system, visible to all operating room personnel. For each of the items registered, the following information is displayed: 1) the type of item (e.g., needle, clamp, sponge); 2) the time the item is placed into (i.e., "checked in") the tracking system; 3) the location of the item being registered; 4) the unique identifier assigned to each item; and 5) the total number of each item currently registered in the tracking system. Once all of the items are registered, two operating room nurses verify the initial count and enter their time-stamped electronic signatures. The surgery then begins. The time for the initial count is 10 minutes.

As each item is used during surgery, the tracking system tracks the current location of the item, as well as whether the item has been removed from the tracking system, or "checked out". For example, as one of the nurses hands a scalpel to a surgeon, the tracking system senses that the scalpel has been moved from the sterile back table, because the camera 1480 over the sterile table will have the count of scalpels reduced by one, while the sensor camera/reader 1460 over the operating table will register an increase by one of the number of scalpels. The time of the transfer of location is also registered. When the surgeon has finished with the scalpel, the nurse returns the scalpel to the sterile back table. The new location for that individual scalpel is registered, as well as time of transfer. In another example, when a 2-0 silk needle is returned by the surgeon to the nurse, the used needle is placed into the sterile sharps automated shape recognition disposal container 1410, on the back table. The imaging device in the sharps container identifies the discarded needle as a 2-0 silk needle, and the tracking system registers the new location and time of deposition of the 2-0 silk needle into the sharps container. The auxiliary display on the sterile sharps container notes the addition of the 2-0 needle to the container, and registers the current total of 4 needles in the container. Similarly, a discarded sponge is dropped by the circulating nurse into a non-sterile sponge disposal unit 1580 on the floor. As the sponge passes into the container, the camera/reader scans the sponge, and the tracking system registers the sponge as off the field, or "checked out" by the circulating nurse.

For each surgical item, each of these steps is performed. During the operation, the system software continuously tracks the surgical items that have been registered with the tracking system. For example, if 50 clamps, 50 forceps, 70 scalpel blades, 70 needles, and 200 sponges have been registered, the system maintains continuous track of the location of each item registered. At any one time, of 70 needles registered, there may be 60 needles located on the sterile back table, one needle in the surgeon's hand on the operating table, and 9 needles that have been placed in the sharps disposable container.

There is a change in personnel twice during the surgery. During each of those times, the tracking system display unit 1550 is checked to verify that all surgical items are accounted for, and two operating room personnel verify the current count and enter their time-stamped electronic signatures. The time for this "count" and verification process takes two minutes.

At the end of the surgery, prior to wound closure, a nurse checks the tracking system display unit, and finds that the current counts are correct, and no surgical items are missing. The two operating room nurses responsible for the count both verify the tracking system display monitor counts by entering their time-stamped electronic signatures. The operating surgeons then close the wound and the surgery is successfully completed.

III. Automated Incorrect Count

The operation initially proceeds as in Example II above, except that 60 minutes into the operation an alarm sounds. After checking the display unit, it is determined that an item is missing. The operating room personnel check the information provided on display unit 1550 for the identification of the item, and it is determined that a 5-0 needle is missing. The display unit also shows that the particular 5-0 needle was last registered as being present on the operating table. The nurse locates the 5-0 needle underneath a fold in the surgical drapes. The needle is then placed into the sterile sharps automated shape recognition disposal container 1410, which identifies the needle as a 5-0 needle. The tracking system display unit then registers the time-stamped new location of the missing 5-0 needle. The total needle count is determined to be correct.

The two operating room nurses responsible for the count both verify the tracking system display monitor counts by entering their time-stamped electronic signatures. The operating surgeons then close the wound and the surgery is successfully completed.

IV. Automated Shape Recognition of Surgical Sharp Objects

Seven types of surgical needles were evaluated using automated shape recognition. The seven needle types included an Ethicon™ 2 Prolene™ 65 mm TP-1 tapered needle, an Ethicon™ 7-0 Prolene™ 9 mm BV-1 tapered needle, an Ethicon™ 2-0 Silk 26 mm SH tapered needle, an Ethicon™ 2-0 Temporary pacing wire 22 mm BB-1 tapered needle, a SKS-3 89 mm straight cutting needle, a Medtronic™ Streamline Unipolar temporary atrial pacing lead, and a Deknatel™ 3-0 17.4 mm Tevdek® polyester fiber AT-2½ circle tapered needle.

The seven needle types were programmed into the Cognex™ Insight-Explorer™ Vision machine vision software. A Cognex™ Insight Micro Smart Camera™, vision camera was mounted above a platform. The needles were placed one by one onto a platform which was backlit by a battery operated light. The seven needles were placed sequentially on the platform.

The machine vision software was able to count only the new additions of needle, by obtaining images of the platform every 80 milliseconds. When a new needle was added to the field of view, comparison of the image obtained just prior to the addition of the new needle with the image obtained after the addition of the new needle was made. The images were then subtracted from each other. The machine vision software was able to identify only the newly added needle, as the previously identified needles were discounted. This method worked even as the needles were dropped on top of each other, such that the needles were overlapping.

The prototype was able to correctly identify the type of needle approximately 99% of the time, even when the needles were overlapping.

V. Automated Shape Recognition of Surgical Sharp Objects with a Disposable Sharps Container A tracking system as disclosed in FIGS. 14 and 15 which includes sterile sharps automated shape recognition disposal container 1410 is used to track the surgical items used for a surgical procedure. At the start of the surgical procedure, seven different types of surgical needles are programmed into the system's automated shape recognition software program. As the nurses prepare for the surgery, they register each package of needles to be used with the tracking system, using sterile hand-held scanner 1570. As each package of needles is registered using the barcode on the outside of the package, the nurses double check the information as it appears on the display unit 1550 of the tracking system, visible to the operating room personnel. For each of the items registered, the following information is displayed: 1) the type of needle; 2) the time the package of needles is registered by the tracking system; 3) the location of the package of needles being registered; 4) a unique identifier assigned to each package of needles; and 5) the total number of each individual item currently registered in the sensor system (e.g., a package of five 4-0 needles registers as a total count of five individual 4-0 needles). Once all of the needles and other surgical items have been registered, two operating room personnel verify the initial count and enter their time-stamped electronic signatures. The surgery then begins.

A total of three of the five 4-0 needles is used during the procedure. As the three 'used' needles are placed individually into the sterile sharps automated shape recognition disposal container 1410, equipped with imaging device 1420, the surgical sharp object automated shape recognition module identifies each needle correctly as a "4-0" as it is dropped into the container by an operating room nurse. The tracking system display unit registers all three needles as being located in the disposable container, along with a time-stamp of the time the needles were placed into the container.

At the conclusion of the procedure, the tracking system display unit indicates that two of the 4-0 needles are located on the sterile back table, as detected by the overhead mounted camera 1480. The display unit also indicates that three of the 4-0 needles are located in the sterile sharps automated shape recognition disposal container 1410. Prior to suturing the wound closed, the needle count (and remainder of the surgical item count, e.g., instruments, other types of needles, and sponges or lap pads) is determined to be correct. The two operating room nurses responsible for the count both verify the tracking system display unit counts by entering their time-stamped electronic signatures. The operating surgeons then close the wound and the surgery is successfully completed.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. It is also to be understood that the terminology used herein is for the purpose of describing particular embodiments only, and is not intended to be limiting, since the scope of the present invention will be limited only by the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A system for intra-operatively identifying a surgical sharp object, the system comprising:
   an intra-operative imaging device for obtaining intra-operative surgical sharp object image data comprising one or more of a shape, size or outline of at least one surgical sharp object; and
   a surgical sharp object automated shape recognition module comprising a processor, a database of pre-existing surgical sharp object image data comprising a shape of at least one surgical sharp object, wherein the automated shape recognition module is configured to identify a surgical sharp object from the intra-operative surgical sharp object image data by comparing the intra-operative surgical sharp object image data with the pre-existing surgical sharp object image data; wherein the surgical sharp object is a needle and a curve formed by a certain size of the needle is used to identify the needle via the automated shape recognition module.

2. The system according to claim 1, wherein the intra-operative imaging device is part of a surgical sharp object disposal container and wherein the intra-operative imaging device is configured to obtain the intra-operative surgical sharp object image data of at least one surgical sharp object within the disposal container.

3. The system according to claim 2, wherein the surgical sharp object automated shape recognition module is part of the surgical sharp object disposal container.

4. The system according to claim 3, wherein the surgical sharp object automated shape recognition module is configured to dynamically identify the surgical sharp object.

5. The system according to claim 1, wherein the surgical sharp object automated shape recognition module comprises an assisted identification algorithm.

6. The system according to claim 1, wherein the intra-operative imaging device is positioned to image surgical sharp objects placed onto a sterile table.

7. The system according to claim 1, wherein the intra-operative imaging device is a hand-held imaging device.

8. The system according to claim 1, wherein the system is configured to track a surgical sharp object.

9. The system according to claim 1, wherein the system further comprises one or more detectors.

10. The system according to claim 1, wherein the system is further configured to identify surgical sponge identifier labels.

11. The system according to claim 1, wherein the system further comprises a display unit.

12. The system according to claim 1, wherein the intra-operative imaging device is configured to obtain the surgical sharp object image data before, during and after a surgical procedure.

13. The system according to claim 1, wherein the intra-operative surgical sharp object image data comprises still image or video image data.

14. The system according to claim 1, wherein identifying a surgical sharp object from the intra-operative surgical sharp object image data comprises a step of manipulating the intra-operative surgical sharp object image data to reduce noise or performing binarization.

15. The system according to claim 1, wherein identifying a surgical sharp object from the intra-operative surgical sharp object image data comprises pixel counting, thresholding, segmentation, pattern recognition, detection of an angle or curve, measurement of an area or size, determination of an aspect ratio, edge detection, outline or silhouette detection, color recognition, template matching, or combinations thereof.

16. The system according to claim 1, wherein identifying a surgical sharp object from the intra-operative surgical sharp object image data comprises employing pre-existing surgical sharp object data in an automated shape recognition protocol.

17. The system according to claim 1, wherein the obtained intra-operative surgical sharp object image data comprises the shape of the at least one surgical sharp object.

18. A method of intra-operatively identifying a surgical sharp object, the method comprising:
   obtaining a surgical sharp object from an operative sterile field;
   imaging the surgical sharp object with an intra-operative imaging device to obtain image data comprising one or more of a shape, size or outline of at least one surgical sharp object; and
   forwarding the image data to a surgical sharp object automated shape recognition module comprising a processor, a database of pre-existing surgical sharp object image data comprising a shape of at least one surgical sharp object, wherein the automated shape recognition module is configured to identify the surgical sharp object from the intra-operative surgical sharp object image data by comparing the intra-operative surgical sharp object image data with the pre-existing surgical sharp object image data; wherein the surgical sharp object is a needle and a curve formed by a certain size of the needle is used to identify the needle via the automated shape recognition module.

19. A surgical sharp object disposal container comprising:
   an intra-operative imaging device for obtaining intra-operative surgical sharp object image data comprising one or more of a shape, size or outline of at least one surgical sharp object; and
   a surgical sharp object automated shape recognition module comprising a processor, a database of pre-existing surgical sharp object image data comprising a shape of at least one surgical sharp object, wherein the automated shape recognition module is configured to identify a surgical sharp object from the intra-operative surgical sharp object image data by comparing the intra-operative surgical sharp object image data with the pre-existing surgical sharp object image data; wherein the surgical sharp object is a needle and a curve formed by a certain size of the needle is used to identify the needle via the automated shape recognition module.

* * * * *